(12) United States Patent
Kwon et al.

(10) Patent No.: US 12,636,680 B2
(45) Date of Patent: May 26, 2026

(54) IMAGING DEVICES HAVING PIEZOELECTRIC TRANSCEIVERS WITH HARMONIC CHARACTERISTICS

(71) Applicant: Exo Imaging, Inc., Santa Clara, CA (US)

(72) Inventors: Haesung Kwon, Austin, TX (US); Brian Bircumshaw, Orinda, CA (US); Sandeep Akkaraju, Wellesley, MA (US)

(73) Assignee: Exo Imaging, Inc., Santa Clara, CA (US)

( * ) Notice: Subject to any disclaimer, the term of this patent is extended or adjusted under 35 U.S.C. 154(b) by 234 days.

(21) Appl. No.: 18/514,989

(22) Filed: Nov. 20, 2023

(65) Prior Publication Data

US 2024/0082876 A1     Mar. 14, 2024

Related U.S. Application Data

(60) Division of application No. 17/364,397, filed on Jun. 30, 2021, now Pat. No. 11,819,881, which is a
(Continued)

(51) Int. Cl.
B06B 1/06 (2006.01)
A61B 8/00 (2006.01)
(Continued)

(52) U.S. Cl.
CPC .......... B06B 1/0603 (2013.01); A61B 8/4483 (2013.01); B06B 2201/76 (2013.01);
(Continued)

(58) Field of Classification Search
None
See application file for complete search history.

(56) References Cited

U.S. PATENT DOCUMENTS 4,549,107 A    10/1985  Kaneko et al.
4,628,573 A    12/1986  Hamada et al.
(Continued)

FOREIGN PATENT DOCUMENTS

CN        101933814 A      1/2011
CN        102577436 A      7/2012
(Continued)

OTHER PUBLICATIONS

Aabid, A Systematic Review of Piezoelectric Materials and Energy Harvesters for Industrial Applications, Sensors, (Year: 2021).*
(Continued)

*Primary Examiner* — James R Hulka
*Assistant Examiner* — Vikas Atmakuri
(74) *Attorney, Agent, or Firm* — Morgan, Lewis & Bockius LLP

(57)      ABSTRACT

A micromachined ultrasonic transducer (MUT) which comprises a first piezoelectric layer and a second piezoelectric layer. The first piezoelectric layer is disposed between a first electrode and a second electrode. The second piezoelectric layer is disposed between the second electrode and a third electrode. At least the first electrode has first and second ends along a first axis, one or more of which is defined by a radius of curvature R. A second axis normal to the first passes through a midpoint of the first axis. A half-width of the first electrode is defined by a length L measured from the midpoint, in the direction of the second axis, to an outer perimeter of the first electrode. A total width of the first electrode at its narrowest point along the first axis is at most 2L such that the first electrode has a concave shape. R/L is greater than 1.

21 Claims, 20 Drawing Sheets

Related U.S. Application Data continuation-in-part of application No. PCT/US2021/025109, filed on Mar. 31, 2021, and a continuation-in-part of application No. 17/218,656, filed on Mar. 31, 2021, now Pat. No. 11,951,512.

(51) Int. Cl.
   *H10N 30/853*          (2023.01)
   *H10N 30/857*          (2023.01)

(52) U.S. Cl.
   CPC ....... *H10N 30/853* (2023.02); *H10N 30/8542* (2023.02); *H10N 30/8548* (2023.02); *H10N 30/8554* (2023.02); *H10N 30/857* (2023.02)

(56)                References Cited

U.S. PATENT DOCUMENTS

| | | | |
|---|---|---|---|
| 6,676,602 | B1 | 1/2004 | Barnes et al. |
| 10,589,317 | B2 | 3/2020 | Hajati |
| 2002/0109436 | A1 | 8/2002 | Peng et al. |
| 2002/0124369 | A1 | 9/2002 | Gauchet |
| 2003/0055308 | A1 | 3/2003 | Friemel et al. |
| 2004/0174773 | A1 | 9/2004 | Thomenius et al. |
| 2005/0146247 | A1 | 7/2005 | Fisher et al. |
| 2005/0203397 | A1 | 9/2005 | Degertekin |
| 2009/0010459 | A1 | 1/2009 | Garbini et al. |
| 2010/0225204 | A1 | 9/2010 | Hamann et al. |
| 2010/0256501 | A1 | 10/2010 | Degertekin |
| 2012/0250454 | A1 | 10/2012 | Rohling et al. |
| 2013/0293065 | A1 | 11/2013 | Hajati et al. |
| 2013/0294201 | A1 | 11/2013 | Hajati |
| 2015/0265245 | A1 | 9/2015 | Von Ramm et al. |
| 2016/0107194 | A1 | 4/2016 | Panchawagh et al. |
| 2016/0136687 | A1 | 5/2016 | Lewis, Jr. et al. |
| 2017/0209121 | A1 | 7/2017 | Davis, Sr. et al. |
| 2017/0322290 | A1 | 11/2017 | Ng et al. |
| 2017/0368574 | A1 | 12/2017 | Sammoura et al. |
| 2019/0316958 | A1* | 10/2019 | Akkaraju ............... G01S 15/899 |
| 2020/0045475 | A1 | 2/2020 | Tamura et al. |
| 2021/0278927 | A1* | 9/2021 | Jennings ................. H10N 30/87 |

FOREIGN PATENT DOCUMENTS

| | | | |
|---|---|---|---|
| CN | 103959818 | A | 7/2014 |
| CN | 104771190 | A | 7/2015 |
| CN | 104887264 | A | 9/2015 |
| CN | 106999163 | A | 8/2017 |
| CN | 104984890 | | 12/2017 |
| CN | 110545731 | A | 12/2019 |
| EP | 3360617 | | 3/2020 |
| IL | 277896 | | 11/2020 |
| IL | 277897 | | 11/2020 |
| JP | H06350155 | A | 12/1994 |
| JP | 2002026681 | | 2/2002 |
| JP | 2005210710 | | 8/2005 |
| JP | 2005342337 | | 12/2005 |
| JP | 2007110281 | | 4/2007 |
| JP | 2008510324 | A | 4/2008 |
| JP | 2010507932 | | 3/2010 |
| JP | 2010519749 | | 6/2010 |
| JP | 2013123150 | A | 6/2013 |
| JP | 2014000122 | A | 1/2014 |
| JP | 2014127921 | A | 7/2014 |
| JP | 2015099864 | | 5/2015 |
| JP | 2015521409 | A | 7/2015 |
| JP | 2016503312 | A | 2/2016 |
| JP | 2018502467 | A | 1/2018 |
| KR | 1020150048666 | | 5/2015 |
| KR | 1020170029497 | | 3/2017 |
| TW | 201018251 | A | 5/2010 |
| WO | WO-2005120355 | | 12/2005 |
| WO | WO-2009088307 | | 7/2009 |
| WO | 2011/033887 | A1 | 3/2011 |
| WO | WO-2014066006 | | 5/2014 |
| WO | WO-2016007250 | | 1/2016 |
| WO | WO-2016175013 | | 11/2016 |
| WO | WO-2017025438 | | 2/2017 |
| WO | WO-2019199397 | | 10/2019 |
| WO | WO-2020230443 | | 11/2020 |

OTHER PUBLICATIONS

Extended European Search Report for Application No. 24158305.3 dated May 3, 2024, 11 pages.

Extended European Search Report for Application No. 21935388.5, dated Oct. 30, 2024, 9 pages.

Extended European Search Report for Application No. 21935414.9, dated Feb. 13, 2025, 11 pages.

Covaci, Piezoelectric Energy Harvesting Solutions: A Review, Sensors (Year: 2020).

* cited by examiner

IMAGING DEVICES HAVING PIEZOELECTRIC TRANSCEIVERS WITH HARMONIC CHARACTERISTICS

CROSS-REFERENCE

The present application is a division of U.S. patent application Ser. No. 17/364,397, filed Jun. 30, 2021, which is a continuation-in-part of U.S. patent application Ser. No. 17/218,656, filed Mar. 31, 2021, and is also a continuation-in-part of PCT Application No. PCT/US2021/025109, filed Mar. 31, 2021, the contents of which are fully incorporated herein by reference.

The subject matter of this application is related to that of: U.S. patent application Ser. No. 16/833,333; U.S. patent application Ser. No. 16/837,800; U.S. Pat. Nos. 10,656,007; 10,648,852; and U.S. application Ser. No. 17/218,656, the contents of which are fully incorporated herein by reference.

BACKGROUND

Technical Field

The present invention relates to imaging devices and, more particularly, to imaging devices having micromachined ultrasound transducers (MUTs) that exhibit enhanced pressure amplitude and frequency response behavior when driven at fundamental and harmonic frequencies.

Background

A non-intrusive imaging system for imaging internal organs of a human body and displaying images of the internal organs transmits signals into the human body and receives signals reflected from the organs. Typically, transducers, such as capacitive transducers (cMUTs) or piezoelectric transducers (pMUTs), that are used in an imaging system are referred to as transceivers and some of the transceivers are based on photo-acoustic or ultrasonic effects.

In general, a MUT includes two or more electrodes and the topology of the electrodes affects both electrical and acoustic performances of the MUT. For instance, the amplitude of acoustic pressure generated by a pMUT increases as the size of the electrodes increase, to thereby improve the acoustic performance of the pMUT. However, as the size of the electrodes increase, the capacitance also increases to degrade the electrical performance of the pMUT. In another example, the amplitude of acoustic pressure at a vibrational resonance frequency of the pMUT is affected by the shape of the electrodes. As such, there is a need for methods for designing electrodes to enhance both acoustical and electrical performances of the transducers.

SUMMARY

In an aspect, a micromachined ultrasonic transducer (MUT) is disclosed. The MUT comprises at least a first piezoelectric layer and a second piezoelectric layer. The first piezoelectric layer is disposed between a first electrode and a second electrode. The second piezoelectric layer is disposed between the second electrode and a third electrode. At least the first electrode has first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its narrowest point along the first axis is at most 2L such that the first electrode has a concave shape. R/L is greater than 1.

In some embodiments, the first axis extends along a direction where the first electrode has a longest dimension.

In some embodiments, the second axis extends along a direction where the first electrode has a shortest dimension.

In some embodiments, the piezoelectric layer is formed of at least one of PZT, KNN, PZT-N, PMN-Pt, AIN, Sc-AIN, ZnO, PVDF, and LiNiO$_3$.

In an aspect, a micromachined ultrasonic transducer (MUT) is disclosed. The MUT comprises a plurality of piezoelectric layers comprising M piezoelectric layers. The MUT also comprises a plurality of electrodes comprising N electrodes. A piezoelectric layer of the plurality of piezoelectric layers with an index m is disposed between a first electrode with an index m and a second electrode with an index m+1. The index m is associated with a vertical distance of the piezoelectric layer. At least the first electrode having first and second ends along a first axis. One or more of the first end or second end is defined by a radius of curvature R. A second axis passes through a midpoint of the first axis. The second axis is normal to the first axis. A half-width of the first electrode is defined by a length L measured from the midpoint, in the direction of the second axis, to an outer perimeter of the first electrode. A total width of the first electrode at its narrowest point along the first axis is at most 2L such that the first electrode has a concave shape. R/L is greater than 1.

In some embodiments, the first axis extends along a direction where the first electrode has a longest dimension.

In some embodiments, the second axis extends along a direction where the first electrode has a shortest dimension.

In some embodiments, the MUT further comprises a substrate and a membrane suspending from the substrate.

In some embodiments, the piezoelectric layer is formed of at least one of PZT, KNN, PZT-N, PMN-Pt, AIN, Sc-AIN, ZnO, PVDF, and LiNiO$_3$.

In some embodiments, N=M+1.

In an aspect, a micromachined ultrasonic transducer (MUT) is disclosed. The MUT comprises at least a first piezoelectric layer and a second piezoelectric layer. The first piezoelectric layer is disposed between a first electrode and a second electrode. The second piezoelectric layer is disposed between the second electrode and a third electrode. At least the first electrode has first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its widest point along the first axis is at least two times L such that the first electrode has a convex shape. R/L is less than 1.

In some embodiments, the first axis extends along a direction where the first electrode has a longest dimension.

In some embodiments, the second axis extends along a direction where the first electrode has a shortest dimension.

In some embodiments, the MUT further comprises a substrate and a membrane suspending from the substrate.

In some embodiments, the piezoelectric layer is formed of at least one of PZT, KNN, PZT-N, PMN-Pt, AIN, Sc-AIN, ZnO, PVDF, and LiNiO$_3$.

In an aspect, a micromachined ultrasonic transducer (MUT) is disclosed. The MUT comprises a plurality of piezoelectric layers comprising M piezoelectric layers. The MUT also comprises a plurality of electrodes comprising N electrodes. A piezoelectric layer of the plurality of piezoelectric layers with an index m is disposed between a first electrode with an index m and a second electrode with an index m+1. The index m is associated with a vertical distance of the piezoelectric layer. At least the first electrode having first and second ends along a first axis. One or more of the first end or second end is defined by a radius of curvature R. A second axis passes through a midpoint of the first axis. The second axis is normal to the first axis. A half-width of the first electrode is defined by a length L measured from the midpoint, in the direction of the second axis, to an outer perimeter of the first electrode. A total width of the first electrode at its widest point along the first axis is at least two times L such that the first electrode has a convex shape. R/L is less than 1.

In some embodiments, the first axis extends along a direction where the first electrode has a longest dimension.

In some embodiments, the second axis extends along a direction where the first electrode has a shortest dimension.

In some embodiments, the MUT further comprises a substrate and a membrane suspending from the substrate.

In some embodiments, the piezoelectric layer is formed of at least one of PZT, KNN, PZT-N, PMN-Pt, AIN, Sc-AIN, ZnO, PVDF, and $LiNiO_3$.

In some embodiments, N=M+1.

In embodiments, a micromachined ultrasonic transducer (MUT) includes a top electrode. The shape of the top electrode is defined by a major and minor axis, where the major and minor axis intersect at an origin point. Both distal ends of the top electrode, i.e., the ends of the top electrode farthest from the origin in the direction of the major axis, are defined by radius of curvature, R. The characteristic width of the top electrode, L, is measured from the origin, in the direction of the minor axis (i.e., normal to the major axis), to the top electrode outer edge or perimeter. When the ratio of the radius of curvature over the characteristic width, R/L, is more than one, the top electrode is wider at its ends as compared to its width at the middle, and the electrode has a generally concave geometry. When the ratio of the radius of curvature over the characteristic width, R/L, is less than one, the top electrode is narrower at its ends as compared to its width at the middle, and the electrode has a generally convex geometry. As set forth in greater detail herein, whether configured with either concave or convex geometry, electrodes with certain R/L values or within certain value ranges exhibit desirable pressure amplitude and frequency response behavior when driven at fundamental and harmonic frequencies, relative to prior electrode shape designs. The areal density distribution of the concave or convex electrode along an axis has a plurality of local maxima, wherein locations of the plurality of local maxima coincide with locations where a plurality of anti-nodal points at a vibrational resonance frequency are located.

In embodiments, a micromachined ultrasonic transducer (MUT) includes a symmetric convex top electrode. The areal density distribution of the symmetric convex electrode along an axis has a plurality of local maxima, wherein locations of the plurality of local maxima coincide with locations where a plurality of anti-nodal points at a vibrational resonance frequency are located.

In embodiments, a transducer array includes a plurality of micromachined ultrasonic transducers (MUTs). Each of the plurality of MUTs includes a symmetric convex top electrode.

In embodiments, an imaging device includes a transducer array that has a plurality of micromachined ultrasonic transducers (MUTs). Each of the plurality of MUTs includes a symmetric convex top electrode. The areal density distribution of the symmetric convex electrode along an axis has a plurality of local maxima and wherein locations of the plurality of local maxima coincide with locations where a plurality of anti-nodal points at a vibrational resonance frequency are located.

In embodiments, a micromachined ultrasonic transducer (MUT) includes a symmetric concave top electrode. The areal density distribution of the symmetric concave electrode along an axis has a plurality of local maxima, wherein locations of the plurality of local maxima coincide with locations where a plurality of anti-nodal points at a vibrational resonance frequency are located.

In embodiments, a transducer array includes a plurality of micromachined ultrasonic transducers (MUTs). Each of the plurality of MUTs includes a symmetric concave top electrode.

In embodiments, an imaging device includes a transducer array that has a plurality of micromachined ultrasonic transducers (MUTs). Each of the plurality of MUTs includes a symmetric concave top electrode. The areal density distribution of the symmetric concave electrode along an axis has a plurality of local maxima and wherein locations of the plurality of local maxima coincide with locations where a plurality of anti-nodal points at a vibrational resonance frequency are located.

In a first aspect, a micromachined ultrasonic transducer (MUT) is provided. The MUT comprises a first electrode having first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its widest point along the first axis is at least two times L such that the first electrode has a convex shape and R/L is less than 1.

In embodiments, the MUT is a capacitive micromachined ultrasound transducer (cMUT).

In embodiments, the MUT is a piezoelectric micromachined ultrasound transducer (pMUT).

In embodiments, the first axis extends along a direction where the first electrode has a longest dimension.

In embodiments, the second axis extends along a direction where the first electrode has a shortest dimension.

In embodiments, the MUT further comprises a substrate; a membrane suspending from the substrate; a second electrode disposed on the membrane; and a piezoelectric layer disposed on one or more of the first electrode or the second electrode. In some embodiments, the piezoelectric layer comprises a first piezoelectric layer disposed on the second electrode. In some embodiments, the MUT further comprises a third electrode disposed on the first piezoelectric layer; and a second piezoelectric layer disposed on the third electrode, wherein the first electrode is disposed on the second piezoelectric layer. In embodiments, the piezoelectric layer is formed of at least one of PZT, KNN, PZT-N, PMN-Pt, AIN, Sc-AIN, ZnO, PVDF, and $LiNiO_3$.

In another aspect, an imaging device is provided. The imaging device comprises a transducer array including a plurality of micromachined ultrasonic transducers (MUTs), each of the plurality of MUTs comprising a convex electrode.

In another aspect, an MUT is provided. The MUT comprises a first electrode having first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its narrowest point along the first axis is less than 2L such that the first electrode has a concave shape and R/L is greater than 1.

In embodiments, the MUT is a capacitive micromachined ultrasound transducer (cMUT).

In embodiments, the MUT is a piezoelectric micromachined ultrasound transducer (pMUT).

In embodiments, the first axis extends along a direction where the first electrode has a longest dimension.

In embodiments, the second axis extends along a direction where the first electrode has a shortest dimension.

In embodiments, the MUT further comprises a substrate; a membrane suspending from the substrate; a second electrode disposed on the membrane; and a piezoelectric layer disposed on one or more of the first electrode or the second electrode. In some embodiments, the piezoelectric layer comprises a first piezoelectric layer disposed on the second electrode. In some embodiments, the MUT further comprises a third electrode disposed on the first piezoelectric layer; and a second piezoelectric layer disposed on the third electrode, wherein the first electrode is disposed on the second piezoelectric layer. In embodiments, the piezoelectric layer is formed of at least one of PZT, KNN, PZT-N, PMN-Pt, AlN, Sc-AlN, ZnO, PVDF, and LiNiO₃.

In another aspect, an imaging device is provided. The imaging device comprises a transducer array including a plurality of micromachined ultrasonic transducers (MUTs), each of the plurality of MUTs comprising a concave electrode

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION

Figure 1:
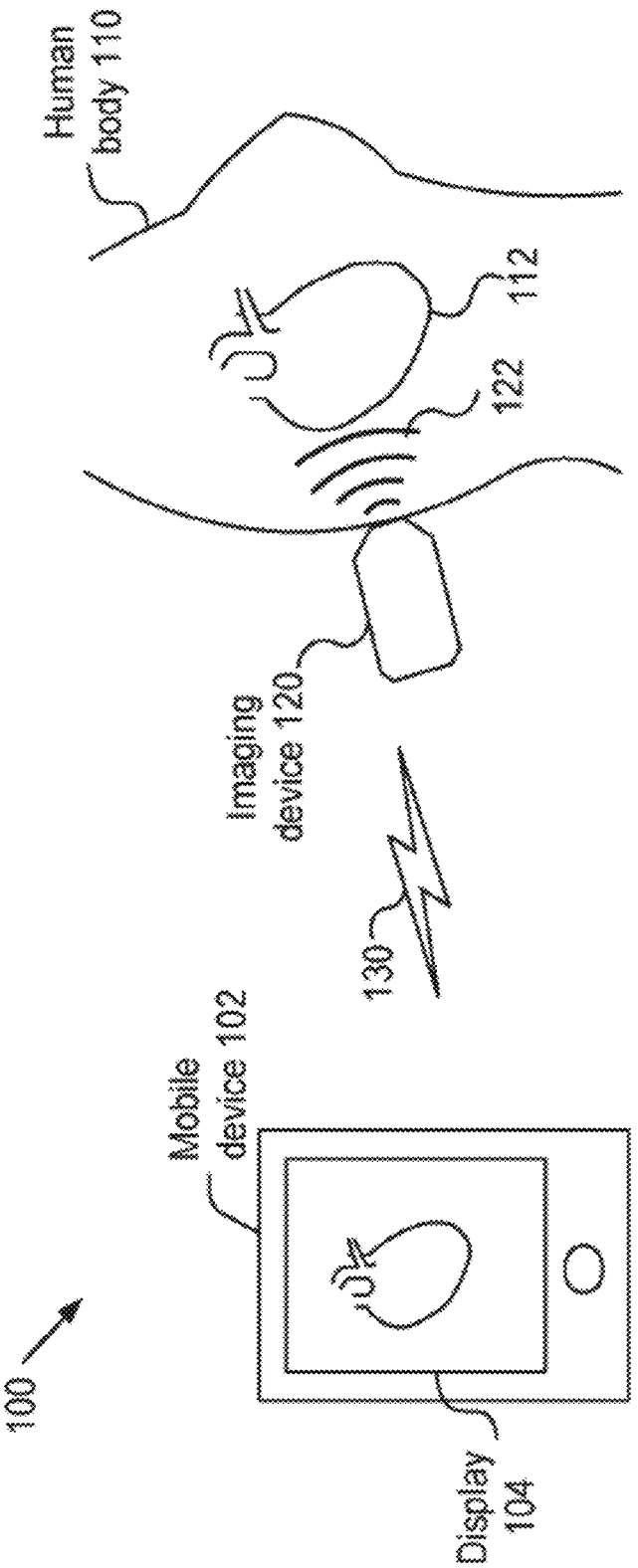
FIG. 1 shows an imaging system according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, or a device.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising"

shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Overview

Disclosed is a multilayer micromachined ultrasonic transducer (MUT). The multilayer MUT may include multiple alternating piezoelectric layers and electrodes (thus being a multilayer pMUT), stacked on top of one another, in a manner such that the piezoelectric layers are "sandwiched" between sets of electrodes. Thus, a given electrode that is not the top layer or the bottom layer may be shared by two piezoelectric layers, being disposed on above a first piezoelectric layer and below a second piezoelectric layer.

Although specific MUT devices disclosed herein are dual-layer, comprising two piezoelectric layers and three conducting layers, or electrodes, MUT devices with additional layers may be designed. As the number of layers increases, the performance of the device may improve. But if the number of layers is too large, the capacitance within the device may increase. As a result, the rise time of signal input may slow down, degrading performance. Generally, a MUT device with M piezoelectric layers may have N conducting layers, where N would equal M+1.

A piezoelectric transducer may transmit acoustic waves into a medium, and receive acoustic waves from the medium, converting the received waves into electrical signals. Piezoelectric materials accumulate electrical charge when mechanically stressed. Piezoelectric materials also exhibit a reverse piezoelectric effect. When an electric field is applied to a piezoelectric material, the applied field causes a mechanical strain. Thus, when a piezoelectric transducer is driven in a transmit (Tx) mode by applying an alternating current (AC) voltage, the oscillating voltage causes the piezoelectric layer to vibrate, producing an acoustic wave. This wave may resonate within a substrate layer disposed under the piezoelectric layer, increasing the output power of the acoustic wave prior to transmission. In a receive (Rx) mode, a reflected acoustic wave causes a mechanical stress on the piezoelectric layer, causing it to accumulate charge. The accumulated charge may generate an electrical signal that may be read by an imaging device.

Augmenting a MUT transducer with additional piezoelectric layers may increase the power of a generated acoustic wave by producing more vibrations when stressed by an AC voltage and may accumulate more charge in response to a stress from a received acoustic wave. Thus, such devices may be both more powerful and more sensitive than single-layer devices.

A device with multiple piezoelectric layers may thus generate acoustic waves with larger output power. As more vibrations are produced when a voltage is applied to a multilayer pMUT, more powerful sound waves may be produced. Conversely, an incident wave may stress the multiple piezoelectric layers, generating a larger signal.

In addition to implementing additional piezoelectric layers, the disclosed MUT device may use convex or concave electrodes that are shaped to exhibit desirable pressure amplitude and frequency responses, when driven at fundamental frequencies and harmonics.

The disclosure defines a MUT aspect ratio, an engineering parameter that may provide information about improved performance at high frequencies. The aspect ratio may be calculated by dividing the length of a long side of an electrode by twice its characteristic half-width (an electrode's short side width at its midpoint). Thus, for electrodes of the same size, a convex electrode may have a smaller aspect ratio than a concave electrode.

This disclosure suggests multilayer MUTs with particular aspect ratios may exhibit increased acoustic wave power, and thus better performance, at high frequencies. A multilayer concave pMUT disclosed herein with a larger aspect ratio than another concave pMUT was shown to have better performance at high frequencies. This result accords with a general relationship between increased R/L in concave pMUTs and improved high-frequency performance.

Multilayer MUT Device

Disclosed herein is a micromachined ultrasonic transducer (MUT), which may be a piezoelectric MUT (pMUT device).

The MUT device may comprise at least two piezoelectric layers. In some embodiments, the MUT device may comprise at least 3 layers, at least 4 layers, at least 5 layers, at least 6 layers, at least 10 layers. The MUT device may comprise at most 3 layers, or at most 4 layers, or at most 5 layers, or at most 6 layers, or at most 10 layers. The MUT device may comprise between 3 and 6 layers, or between 4 and 7 layers, or between 5 and 8 layers, or between 6 and 9 layers, or between 7 and 10 layers. The piezoelectric layers may be of uniform thickness. The piezoelectric layers may be of non-uniform thickness. The piezoelectric layers may all be of different thicknesses. Subsets of piezoelectric layers may have the same thickness but may be distinct in thickness from other subsets.

A piezoelectric layer may be disposed between two electrodes, a second electrode above and a first electrode below. Each piezoelectric layer in the device may be disposed between two electrodes in this manner. Thus, the device may include one more electrode than there are piezoelectric layers, as layers may share electrodes. In some embodiments, the MUT device may comprise at least 3 electrodes, at least 4 electrodes, at least 5 electrodes, at least 6 electrodes, at least 10 electrodes. The MUT device may comprise at most 3 electrodes, or at most 4 electrodes, or at most 5 electrodes, or at most 6 electrodes, or at most 10 electrodes. The MUT device may comprise between 3 and 6 electrodes, or between 4 and 7 electrodes, or between 5 and 8 electrodes, or between 6 and 9 electrodes, or between 7 and 10 electrodes, or between 8 and 11 electrodes.

In some embodiments, at least the first electrode has first and second ends along a first axis. In some embodiments, all of the electrodes have first and second ends along the first axis. In other embodiments, less than half the electrodes have first and second ends along the first axis. In other embodiments, more than half, but fewer than all, of the electrodes have first and second ends along the first axis.

One or more of the first end of an electrode or the electrodes or a second end of the electrode or electrodes may be defined by a radius of curvature R. The first end and the second end may be shaped like portions of circles. The first and second ends may or may not have the same radius of curvature R. The first ends and/or second may additionally be shaped like portions of ovals, triangles, squares, or rectangles, but may not employ sharp edges, which may degrade performance of the MUT. The first ends and/or second ends may be shaped differently. The electrodes may all have the same shape. Some electrodes of the multielectrode MUT may have the same shape, and others may be of another shape. Some or all of the electrodes may each be of different shapes.

The first and second axis may be normal or perpendicular to one another. The second axis may pass through a midpoint of the first axis, and/or vice-versa.

The multilayer MUT may include electrodes that have particular shapes to improve performance. The MUT electrode may be substantially ovular or oblong, with a long side and a short side. The width of the electrode may vary along an axis bisecting the long side of the electrode. For example, close to the midpoint, the electrode may be thinner than on the long ends, creating a concave shape. In other embodiments, the electrode may be thicker in the middle than on the long ends, creating a convex shape.

A half-width of an electrode may be defined by a length L measured from the midpoint, in the direction of the second (or short) axis, to an outer perimeter of the electrode. All of the electrodes may have the same L. One set of electrodes may have the same L, while the other electrodes may have a different value for L. Additionally, some or all of the electrodes may have multiple different values of L.

In some embodiments, the total width of an electrode at its narrowest point along the first axis is less than 2L such that the electrode has a concave shape. The electrode may be one of the first, second, third, fourth, fifth, sixth, seventh, eighth, ninth, tenth, or eleventh electrode. The electrode may be more than one, but less than all, of the first, second, third, fourth, fifth, sixth, seventh, eighth, ninth, tenth, or eleventh electrodes. All of the electrodes may have the same concave shape, with their total widths at their narrowest points along their first axes being less than 2L.

In some embodiments, the total width of an electrode at its widest point along the first axis is at least two times L such that the electrode has a convex shape. The electrode may be one of the first, second, third, fourth, fifth, sixth, seventh, eighth, ninth, tenth, or eleventh electrodes. The electrode may be more than one, but less than all, of the first, second, third, fourth, fifth, sixth, seventh, eighth, ninth, tenth, or eleventh electrodes. All of the electrodes may have the same convex shape, with their total widths at their widest points along their first axes being greater than two times L In some embodiments, all electrodes may be symmetrical. In some embodiments, one or more electrodes may be asymmetrical with respect to the first axis and/or the second axis.

In embodiments where an electrode has a convex shape, the ratio of R to L may be less than 1. For example, the ratio may be less than 0.01, less than 0.1, less than 0.2, less than 0.3, less than 0.4, less than 0.5, less than 0.6, less than 0.7, less than 0.8, less than 0.9, less than 0.99, or less than 0.999. The ratio may be greater than about 0.01, greater than 0.1, greater than 0.2, greater than 0.3, greater than 0.4, greater than 0.5, greater than 0.6, greater than 0.7, greater than 0.8, greater than 0.9, greater than 0.99, or greater than 0.999. The ratio may be between 0 and 0.1, between 0.1 and 0.2, between 0.2 and 0.3, between 0.3 and 0.4, between 0.4 and 0.5, between 0.5 and 0.6, between 0.6 and 0.7, between 0.7 and 0.8, between 0.8 and 0.9, and between 0.9 and 1.

In embodiments where the electrode has a concave shape, the ratio of R to L may be greater than 1. For example, the ratio may be less than 1.01, less than 1.1, less than 1.2, less than 1.3, less than 1.4, less than 1.5, less than 2, less than 5, less than 10, less than 25, less than 50, or less than 100. The ratio may be greater than about 1.01, greater than 1.1, greater than 1.2, greater than 1.3, greater than 1.4, greater than 1.5, greater than 2, greater than 5, greater than 10, greater than 25, greater than 50, or greater than 100. The ratio may be between 1.0 and 1.1, between 1.1 and 1.2, between 1 and 2, between 2 and 5, between 5 and 10, between 10 and 25, between 25 and 50, or between 50 and 100.

In some embodiments, the MUT also includes a substrate and a membrane suspending from the substrate. The substrate may comprise a semiconducting material or may comprise multiple alternating layers of semiconducting materials and insulating materials. For example, the substrate may comprise a silicon layer. The substrate may also comprise alternating layers of silicon and silicon dioxide (i.e., a silicon-on-insulator (SOI) substrate). In other embodiments, the substrate may comprise semiconducting materials such as germanium, silicon-germanium, carbon-doped silicon, carbon-doped silicon-germanium, or another material. In some embodiments, the substrate may include a cavity disposed underneath the MUT's alternating piezoelectric layers and electrodes.

In some embodiments, the membrane may be a silicon layer configured to assist with transmitting and receiving acoustic waves. The membrane may vibrate in response to motion from the piezoelectric elements, after an AC voltage is applied to them, which may in turn may produce the acoustic wave that is transmitted to the subject. When an acoustic wave is reflected, the acoustic wave may disturb the membrane, in turn stressing the piezoelectric layers and causing them to produce electrical signals. These electrical signals may be provided to an imaging device. a In embodiments of the disclosure, the first axis extends along the electrode's longest dimension. In embodiments of the disclosure, the second axis extends along the electrode's shortest dimension.

In embodiments of the disclosure, at least one piezoelectric layer may be formed of at least one of PZT, KNN, PZT-N, PMN-Pt, AlN, Sc-AlN, ZnO, PVDF, and $LiNiO_3$. In some embodiments, all of the piezoelectric materials are formed of the same material. In some embodiments, at least one piezoelectric layer is a composite of one of the aforementioned materials. In some of the embodiments, a first plurality of piezoelectric layers may be formed from one material, and a second plurality may be formed from another material. In some embodiments, all piezoelectric layers are heterogeneous. In some embodiments, a first plurality of piezoelectric layers are homogeneous, and a second plurality of piezoelectric layers are heterogeneous.

In embodiments of the disclosure, a MUT device may have M piezoelectric layers. The MUT device may have N electrodes. As a piezoelectric layer may be "sandwiched" between two electrodes, the number N may be equal to M+1. Generally, for an M-piezoelectric layer MUT device, one may index the piezoelectric layers from 1 to M, where 1 is the layer closest to the substrate and M is the layer furthest from the substrate. For a piezoelectric layer m in this set, adjacent electrodes may be indexed as m and m+1, for electrodes closer to and further away from the substrate, respectively. For example, a second piezoelectric layer may be provided an index of 2, where the electrodes below and above it may be indexed 2 and 3, respectively.

DESCRIPTION OF THE FIGURES

FIG. 1 shows a schematic diagram of an imaging system 100 according to embodiments of the present disclosure. As depicted, the system 100 may include: an imager 120 that generates and transmits pressure waves 122 toward an internal organ 112, such as heart, in a transmit mode/process and receives pressure waves reflected from the internal organ; and a device 102 that sends and receives signals to the imager through a communication channel 130. In embodiments, the internal organ 112 may reflect a portion of the pressure waves 122 toward the imager 120, and the imager 120 may capture the reflected pressure waves and generate electrical signals in a receive mode/process. The imager 120 may communicate electrical signals to the device 102 and the device 102 may display images of the organ or target on a display/screen 104 using the electrical signals.

In embodiments, the imager 120 may be used to get an image of internal organs of an animal, too. The imager 120 may also be used to determine direction and velocity of blood flow in arteries and veins as in Doppler mode imaging and also measure tissue stiffness. In embodiments, the pressure wave 122 may be acoustic waves that can travel through the human/animal body and be reflected by the internal organs, tissue or arteries and veins.

In embodiments, the imager 120 may be a portable device and communicate signals through the communication channel 130, either wirelessly (using a protocol, such as 802.11 protocol) or via a cable (such as USB2, USB 3, USB 3.1, USB-C, and USB thunderbolt), with the device 102. In embodiments, the device 102 may be a mobile device, such as cell phone or iPad, or a stationary computing device that can display images to a user.

In embodiments, more than one imager may be used to develop an image of the target organ. For instance, the first imager may send the pressure waves toward the target organ while the second imager may receive the pressure waves reflected from the target organ and develop electrical charges in response to the received waves.

Figure 2:
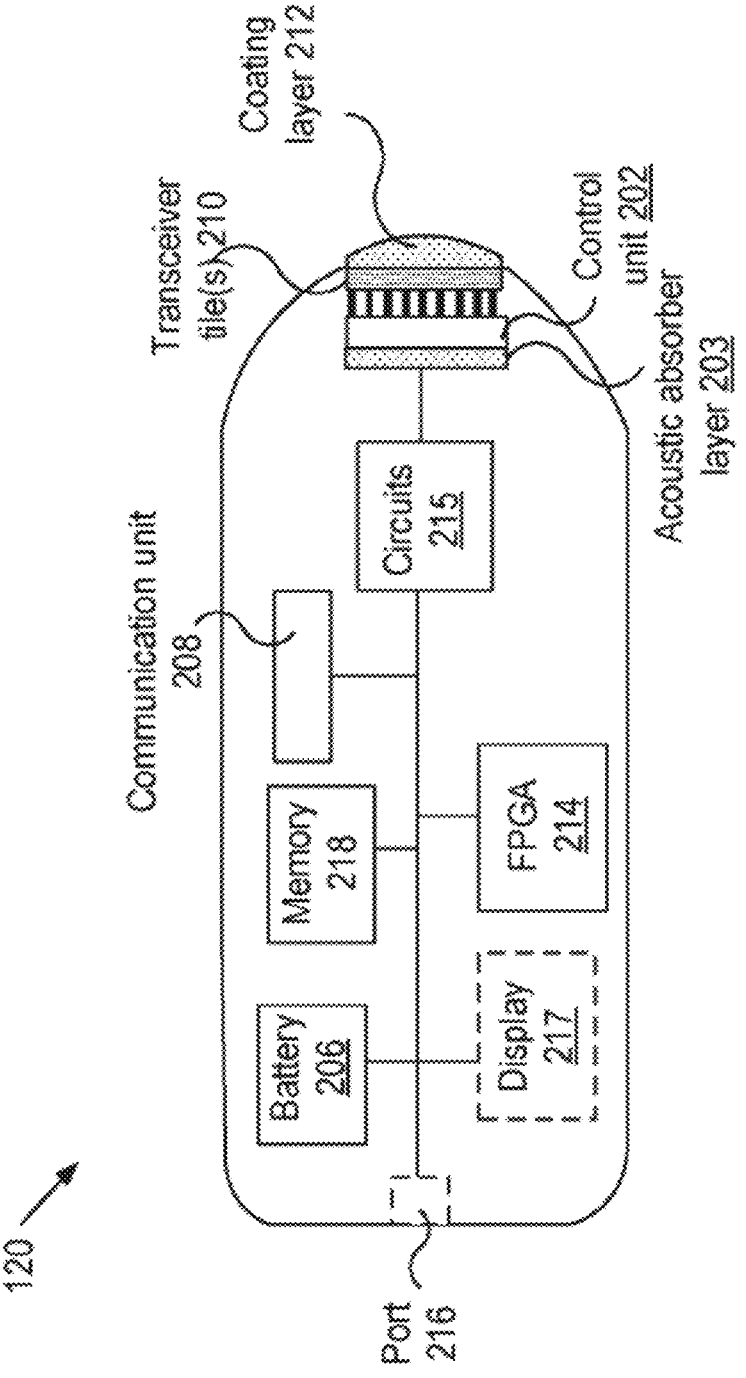
FIG. 2 shows a schematic diagram of an imager according to embodiments of the present disclosure.

FIG. 2 shows a schematic diagram of the imager 120 according to embodiments of the present disclosure. In embodiments, the imager 120 may be an ultrasonic imager. As depicted in FIG. 2, the imager 120 may include: a transceiver tile(s) 210 for transmitting and receiving pressure waves; a coating layer(s) 212 that operate as a lens for setting the propagation direction of and/or focusing the pressure waves and also functions as an acoustic impedance interface between the transceiver tile and the human body 110; a control unit 202, such as ASIC chip (or, shortly ASIC), for controlling the transceiver tile(s) 210 and coupled to the transducer tile 210 by bumps; Field Programmable Gate Arrays (FPGAs) 214 for controlling the components of the imager 120; a circuit(s) 215, such as Analogue Front End (AFE), for processing/conditioning signals; an acoustic absorber layer 203 for absorbing waves that are generated by the transducer tiles 210 and propagate toward the circuit 215; a communication unit 208 for communicating data with an external device, such as the device 102, through one or more ports 216; a memory 218 for storing data; a battery 206 for providing electrical power to the components of the imager; and optionally a display 217 for displaying images of the target organs.

In embodiments, the device 102 may have a display/screen. In such a case, the display may not be included in the imager 120. In embodiments, the imager 120 may receive electrical power from the device 102 through one of the ports 216. In such a case, the imager 120 may not include the battery 206. It is noted that one or more of the components of the imager 120 may be combined into one integral electrical element. Likewise, each component of the imager 120 may be implemented in one or more electrical elements.

In embodiments, the user may apply gel on the skin of the human body 110 before the body 110 makes a direct contact with the coating layer 212 so that the impedance matching at the interface between the coating layer 212 and the human body 110 may be improved, i.e., the loss of the pressure wave 122 at the interface is reduced and the loss of the reflected wave travelling toward the imager 120 is also reduced at the interface. In embodiments, the transceiver tiles 210 may be mounted on a substrate and may be attached to an acoustic absorber layer. This layer absorbs any ultrasonic signals that are emitted in the reverse direction, which may otherwise be reflected and interfere with the quality of the image.

As discussed below, the coating layer 212 may be only a flat matching layer just to maximize transmission of acoustic signals from the transducer to the body and vice versa. Beam focus is not required in this case, because it can be electronically implemented in control unit 202. The imager 120 may use the reflected signal to create an image of the organ 112 and results may be displayed on a screen in a variety of format, such as graphs, plots, and statistics shown with or without the images of the organ 112.

In embodiments, the control unit 202, such as ASIC, may be assembled as one unit together with the transceiver tiles. In other embodiments, the control unit 202 may be located outside the imager 120 and electrically coupled to the transceiver tile 210 via a cable. In embodiments, the imager 120 may include a housing that encloses the components 202-215 and a heat dissipation mechanism for dissipating heat energy generated by the components.

Figure 3A:
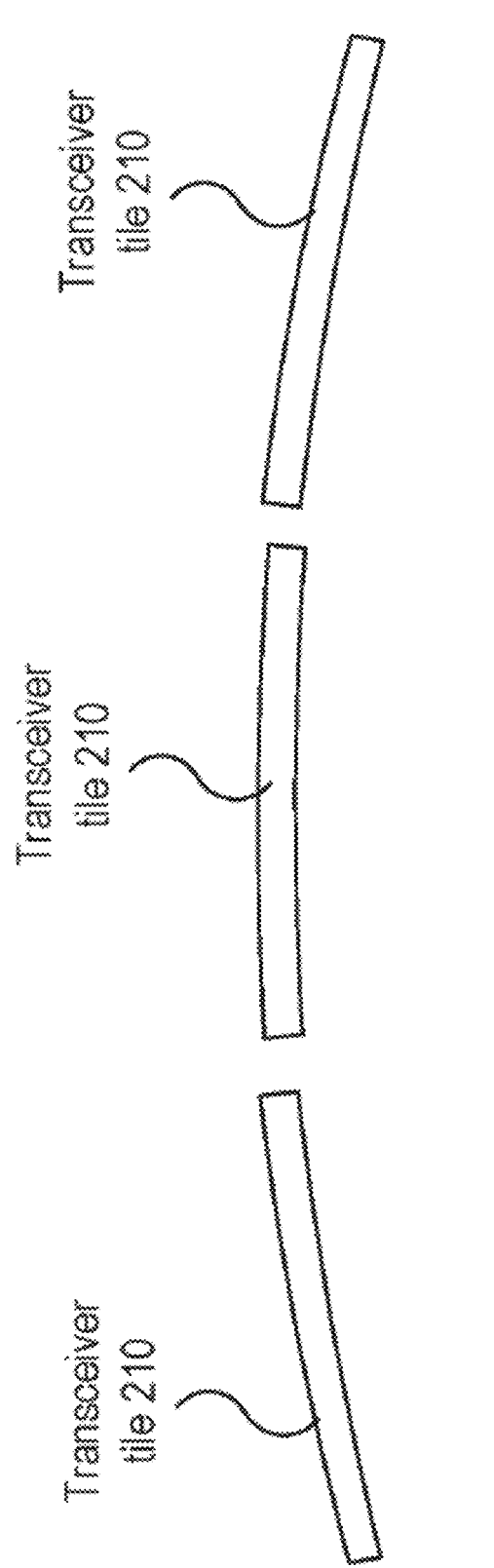
FIG. 3A shows a side view of a transceiver array according to embodiments of the present disclosure.
Figure 3B:
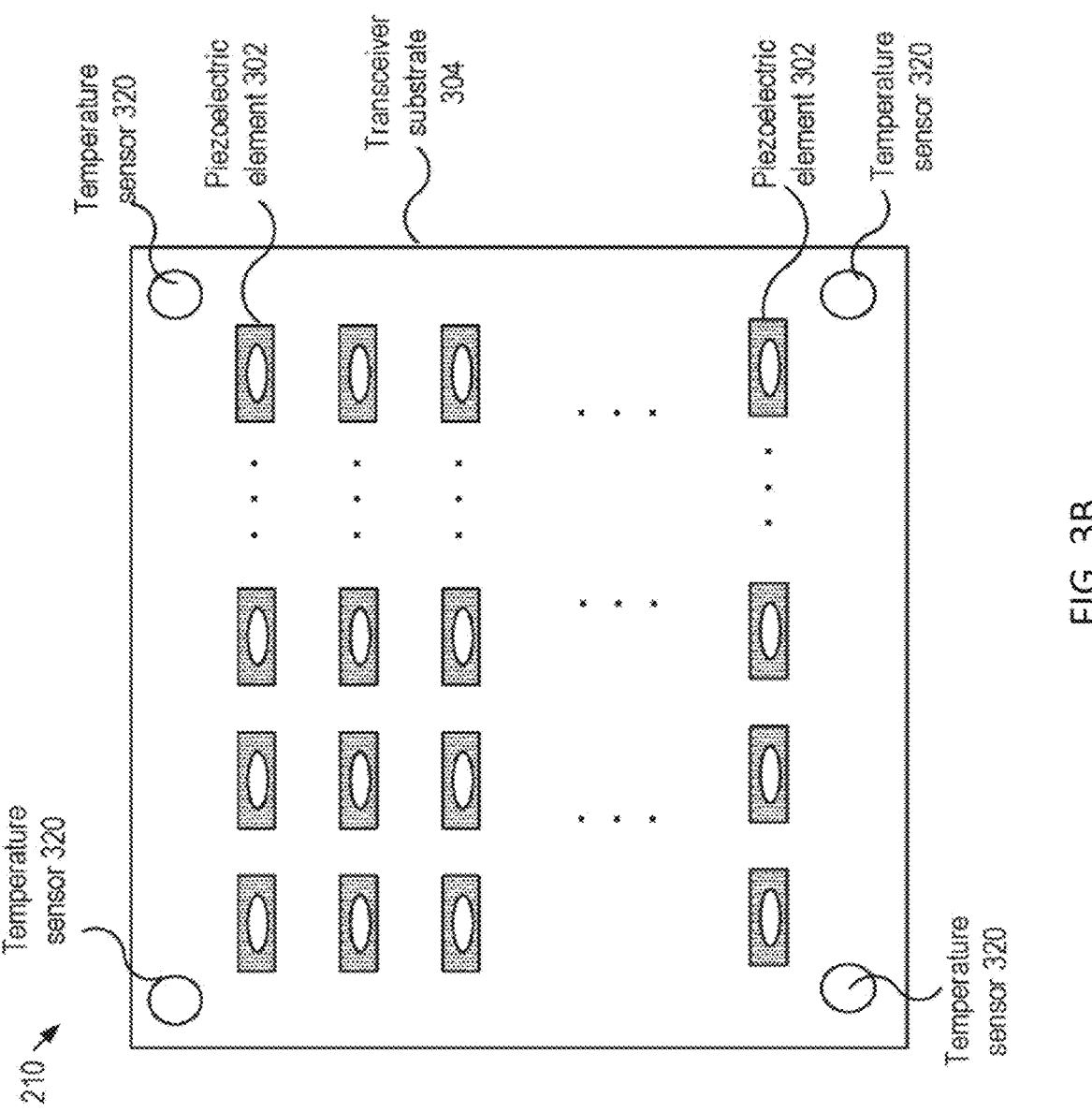
FIG. 3B shows a top view of a transceiver tile according to embodiments of the present disclosure.

FIG. 3A shows a side view of a transceiver array 200 according to embodiments of the present disclosure. FIG. 3B shows a top view of a transceiver tile 210 according to embodiments of the present disclosure. In embodiments, the array 200 may include one or more transceiver tiles 210. As depicted, the transceiver array 200 may include one or more transceiver tiles 210 arranged in a predetermined manner. For instance, as depicted in FIG. 3A, the transceiver tiles (or, shortly tiles) 210 may be physically bent to further form a curved transceiver array and disposed in the imager 120. It should be apparent to those of ordinary skill in the art that the imager 120 may include any suitable number of tiles and the tiles may be arranged in any suitable manner, and each tile 210 may include any suitable number of piezoelectric elements 302 having a concave or convex shape as described in greater detail herein, that are disposed on a transceiver substrate 304. On the substrate 304, one or multiple number of temperature sensors 320 may be placed in order to monitor the temperature of the transceiver tile 210 during operation. In embodiments, the transceiver array 200 may be a micromachined array fabricated from a substrate.

Figure 4A:
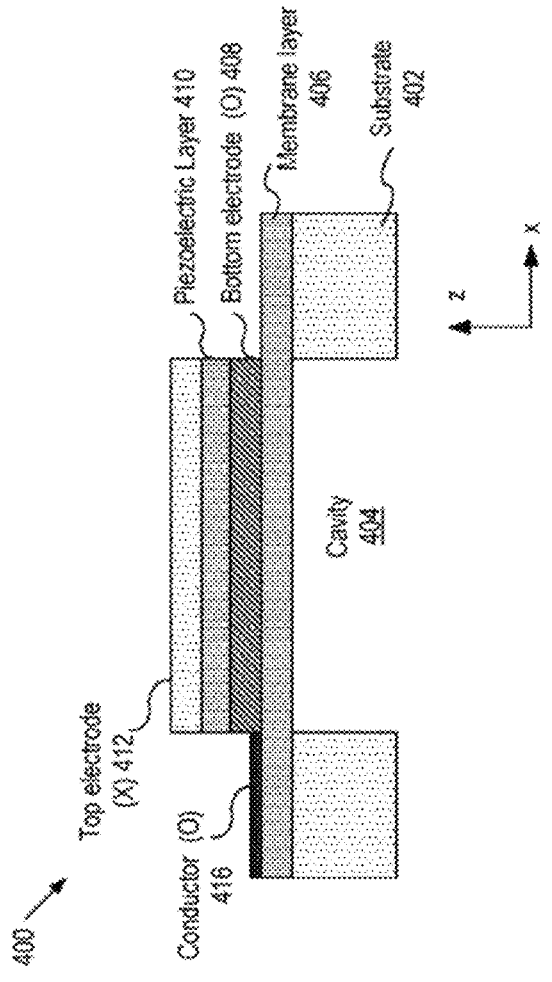
FIG. 4A shows a cross sectional view of a MUT, applicable to a concave or a convex MUT, taken along a direction 4-4 in FIG. 4B and FIG. 4D, according to embodiments of the present disclosure.
Figure 4B:
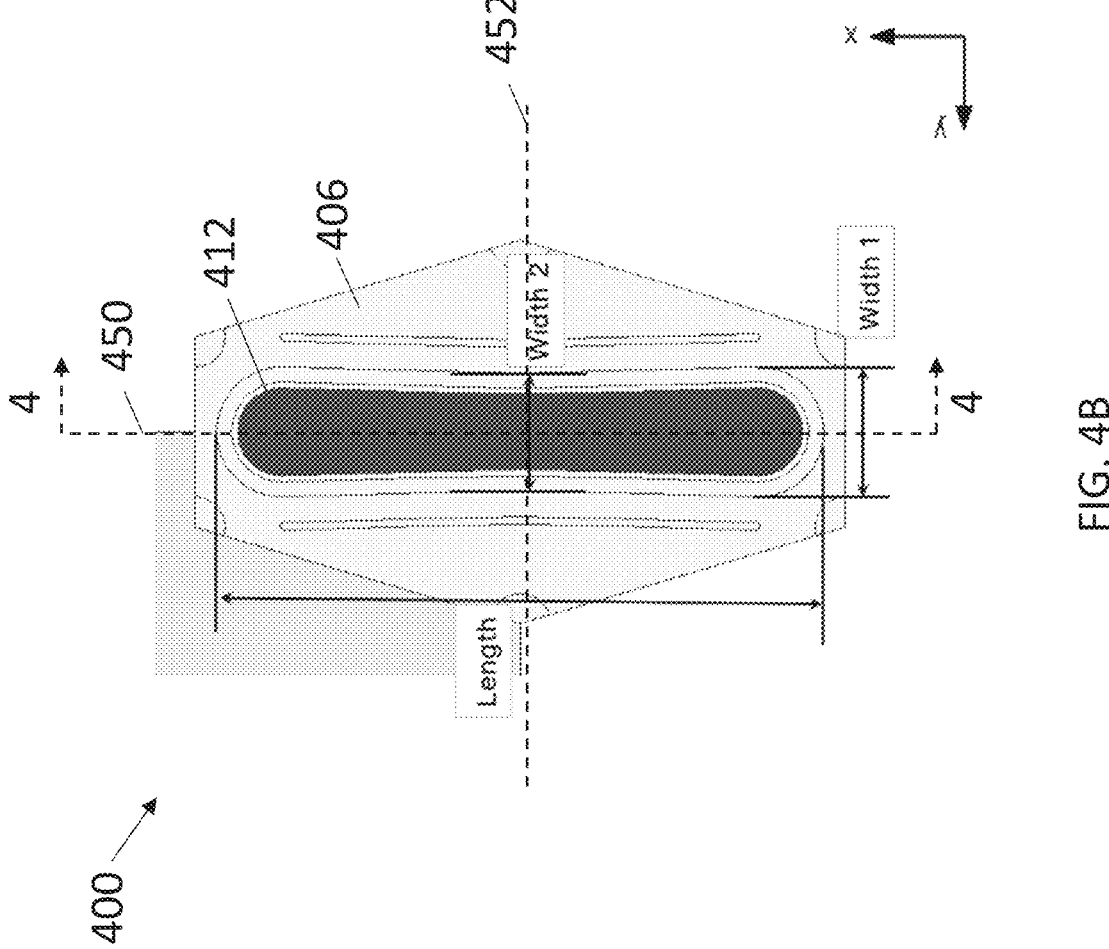
FIG. 4B shows a top view of a concave MUT according to embodiments of the present disclosure.
Figure 4C:
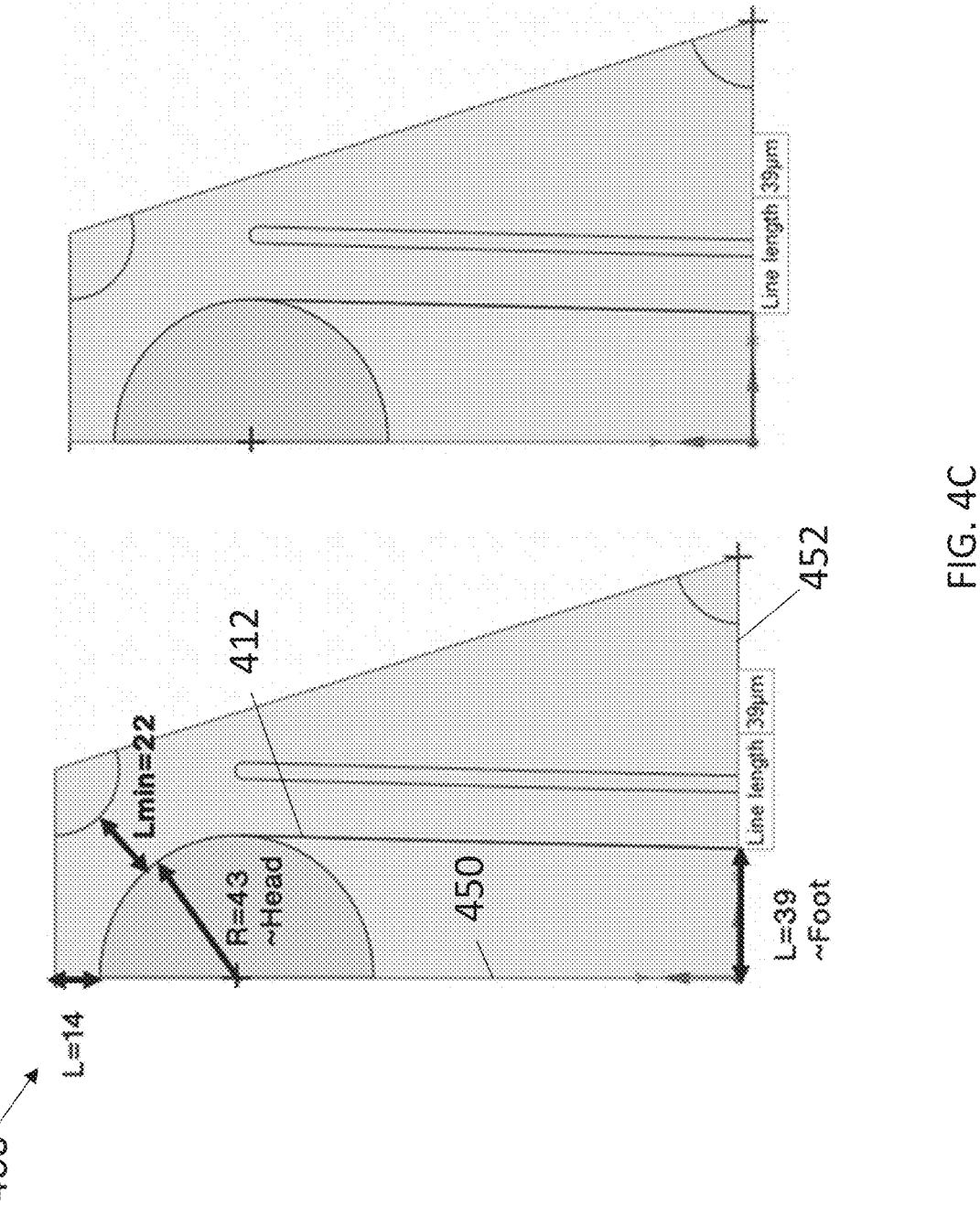
FIG. 4C shows an alternative top view of a concave MUT according to embodiments of the present disclosure.

FIG. 4A shows a cross sectional view of a MUT 400, according to embodiments of the present disclosure. The cross sectional view of FIG. 4A is applicable to a concave or a convex MUT, according to embodiments of the present disclosure. As depicted, the concave or convex MUT may include: a membrane layer 406 suspended from a substrate 402; a first (e.g., bottom) electrode (O) 408 disposed on the membrane layer (or, shortly membrane) 406; a piezoelectric layer 410 disposed on the bottom electrode (O) 408; and a second (e.g., top) electrode (X) 412 disposed on the piezoelectric layer 410.

In embodiments, the substrate 402 and the membrane 406 may be one monolithic body and the cavity 404 may be formed to define the membrane 406. In embodiments, the cavity 404 may be filled with a gas at a predetermined pressure or an acoustic damping material to control the vibration of the membrane 406. In embodiments, the geometrical shape of the projection area of the top electrode 412 may be configured in a generally concave or convex shape having characteristic geometric parameters to control the dynamic performance and capacitance magnitude of the MUT 400.

In embodiments, each MUT 400 may by a pMUT and include a piezoelectric layer formed of at least one of PZT, KNN, PZT-N, PMN-Pt, AlN, Sc—AlN, ZnO, PVDF, and LiNiO₃. In alternative embodiments, each MUT 400 may be a cMUT.

In embodiments, each MUT 400 may include additional electrodes and/or PZE layers. For example, as shown in FIG. 4F, the MUT 400 (be it concave, convex, or otherwise shaped as desired) may include: a membrane layer 406 suspended from a substrate 402; a first electrode (O) 408 disposed on the membrane layer (or, shortly membrane) 406; a first piezoelectric layer 410 disposed on the first electrode (O) 408; a second electrode 414 disposed on the first piezoelectric layer 410; a second piezoelectric layer 410 disposed on the second electrode 414; and a third electrode (X) 412 disposed on the second piezoelectric layer 410. Additional piezoelectric layers 410 and electrodes may be added as desired. In at least some instances, adding additional piezoelectric layers and/or electrodes (i.e., "sandwiching" electrodes and piezoelectric layers) increases the amplitude/dB output of the MUT 400.

In FIGS. 4B-4E and 4G-H, each MUT 400 is shown to have either a concave or convex shape. In embodiments, each concave MUT may include a top electrode that has a concave shape when viewed from the top of the MUT 400. In embodiments, each convex MUT may include a top electrode that has a convex shape when viewed from the top of the MUT 400. Hereinafter, the term shape of the top electrode 412 refers to a two-dimensional shape of the top electrode obtained by projecting the top electrode on to the x-y plane. Also, the shape of the top electrode is called symmetric if the shape is symmetric with respect to the two lines 450 and 452, where the lines 450 and 452 are parallel to the x- and y-axes, respectively, and pass through the midpoint of the top electrode on the x-axis. Also, hereinafter, the x-axis, also referred to herein as the major axis, extends along the direction where the top electrode has the longest dimension. The y-axis, also referred to herein as the minor axis, extends along the direction normal to the x- or major axis in the x-y plane, along the direction where the top electrode has the shortest dimension.

Figure 4D:
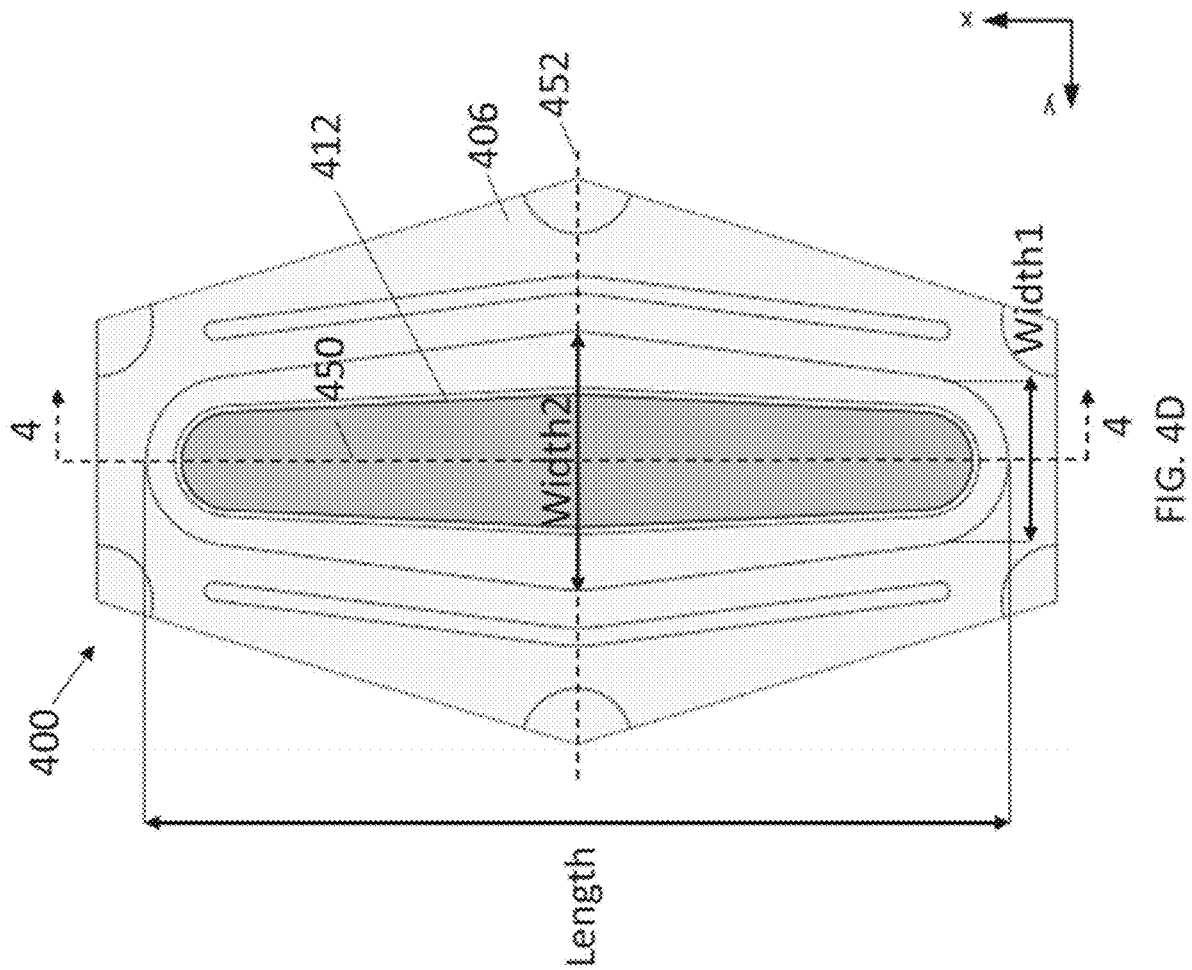
FIG. 4D shows a top view of a convex MUT according to embodiments of the present disclosure.
Figure 4E:
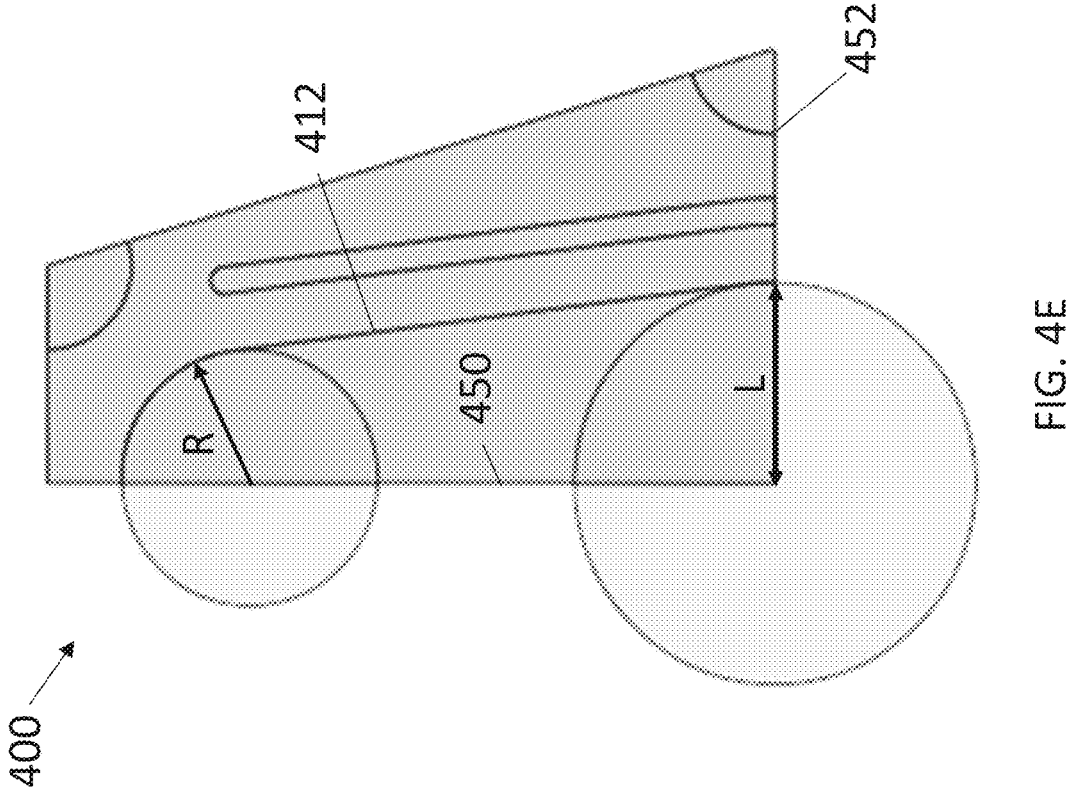
FIG. 4E shows an alternative top view of a convex MUT according to embodiments of the present disclosure.
Figure 4F:
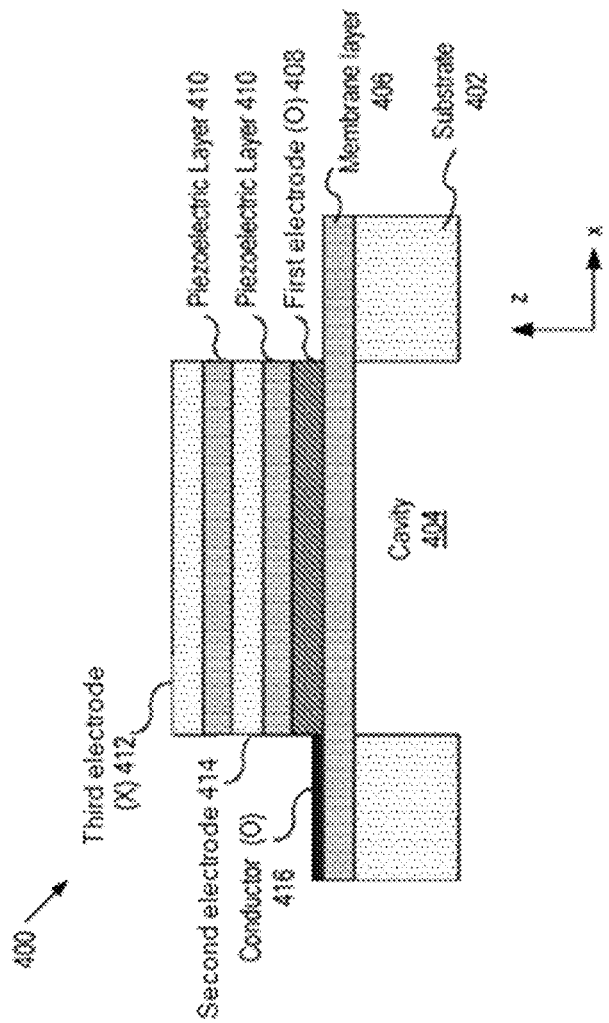
FIG. 4F shows a cross sectional view of another MUT, applicable to a concave or a convex MUT, taken along a direction 4-4 in FIG. 4B and FIG. 4D, according to embodiments of the present disclosure.

Whether the concave MUT of FIGS. 4B-4C and 4G-H or the convex MUT of FIGS. 4D-4E, the shape of the top electrode is defined by a major and minor axis, where the major and minor axis intersect at an origin point. Both distal ends of the top electrode, i.e., the ends of the top electrode farthest from the origin in the direction of the major axis, also referred to herein as the "heads" of the electrode, are defined by a radius of curvature, R. The characteristic half-width of the top electrode, also referred to herein as the "foot" of the electrode, is defined by a length L measured from the origin, in the direction of the minor axis (i.e., normal to the major axis), to the electrode outer edge or perimeter. The total width of the electrode at either its narrowest point (if a concave MUT) or its widest point (if a convex MUT) is two times L (i.e., 2L). Edges of the electrode between the head and foot of the electrode may be curved or straight.

Alternatively, the heads of the electrodes may be straight or be defined by other curvature geometries that are not entirely circular. In at least some instances, it may be beneficial to avoid) geometries that create localized areas of concentrated mechanical stress, which may enable a local mechanical or material failure mode, such as might be created if the head (or foot, for example) were defined by two straight lines converging at a sharp point.

In some embodiments, the head need not be circular, but may also be defined by, without limitation, non-circular curvature such as that of a parabola. Whereas a circular electrode head might be defined by a radius of curvature, R, the relevant parameter for a parabolic-shaped head might be the semilatus rectum of the parabola, defined as twice the distance between the parabola focus and vertex. Furthermore, the perimeter between the head and the foot may be defined either by a straight line or curvature and still be within the scope of this invention.

As illustrated in FIGS. 4B-4C and 4G-4H, when the ratio of the radius of curvature over the characteristic width, R/L, is more than one, the top electrode is wider at its ends, or heads, as compared to its width at the middle, or foot, and the electrode has a generally concave geometry. As one of ordinary skill in the art would appreciate, variations of this concave MUT geometry are possible and still within the scope of this disclosure by varying the R/L ratio, so long as R/L is more than one, i.e., R>L. For example, for a top electrode having a head radius of curvature, R, of 43 micrometers, suitable foot width, L, of between approximately 37 and 41 micrometers would fall within the scope of this disclosure and exhibit the enhanced pressure amplitude and frequency response behavior when driven at fundamental and harmonic frequencies, as will be further described herein. On the other hand, if R/L is too large, whereby the head radius or curvature R is much larger than the foot width, L, the top electrode may not exhibit the desired pressure amplitude and frequency response behavior when driven at fundamental and harmonic frequencies, and can even experience structural failure.

As illustrated in FIGS. 4D-4E, when the ratio of the radius of curvature over the characteristic width, R/L, is less than one, the top electrode is narrower at its ends as compared to its width at the middle, and the electrode has a generally convex geometry. As one of ordinary skill in the art would appreciate, variations of this convex MUT geometry are possible and still within the scope of this disclosure by varying the R/L ratio, so long as R/L is less than one, i.e., R<L. For example, for a top electrode having a head radius of curvature, R, of 43 micrometers, suitable foot width, L, of between approximately 43.1 and 500 micrometers would fall within the scope of this disclosure and exhibit the enhanced pressure amplitude and frequency response behavior when driven at fundamental and harmonic frequencies, as will be further described herein. On the other hand, if R/L is too small, whereby the head radius or curvature R is much smaller than the foot width, L, the top electrode suffers from undesirable pressure amplitude and frequency response behavior when driven at fundamental and harmonic frequencies, and can even experience structural failure.

Whether configured with either concave or convex geometry, electrodes with certain R/L values or within certain R/L value ranges exhibit desirable pressure amplitude and frequency response behavior when driven at fundamental and harmonic frequencies, relative to certain prior electrode shape designs. The areal density distribution of the concave or convex electrode along an axis has a plurality of local maxima, wherein locations of the plurality of local maxima coincide with locations where a plurality of anti-nodal points at a vibrational resonance frequency are located. In general, the acoustic pressure performance, which refers to the energy of an acoustic pressure wave generated by each MUT at a frequency, may increase as the peak amplitude of the MUT increases at the frequency.

The ratio or R/L may be driven by the desired behavior of the MUT. Changing the R/L parameter of the electrode (and therefore, the geometry of the electrode) varies the pressure amplitude and frequency response behavior of the electrode. R/L may be large or small without limitation, so long as the electrode exhibits the desired pressure amplitude and/or frequency response behavior. The design requirements of the particular transducer, which may be dictated by factors such as transducer end use case (e.g., industrial, medical diagnosis, etc.), power requirements, operating mode requirements, etc., inform whether the pressure amplitude and frequency response exhibited by a particular R/L geometry is acceptable or desirable. Additional considerations such as fabrication and material capabilities may further limit the desirable or available range acceptable R/L ranges.

Figure 4G:
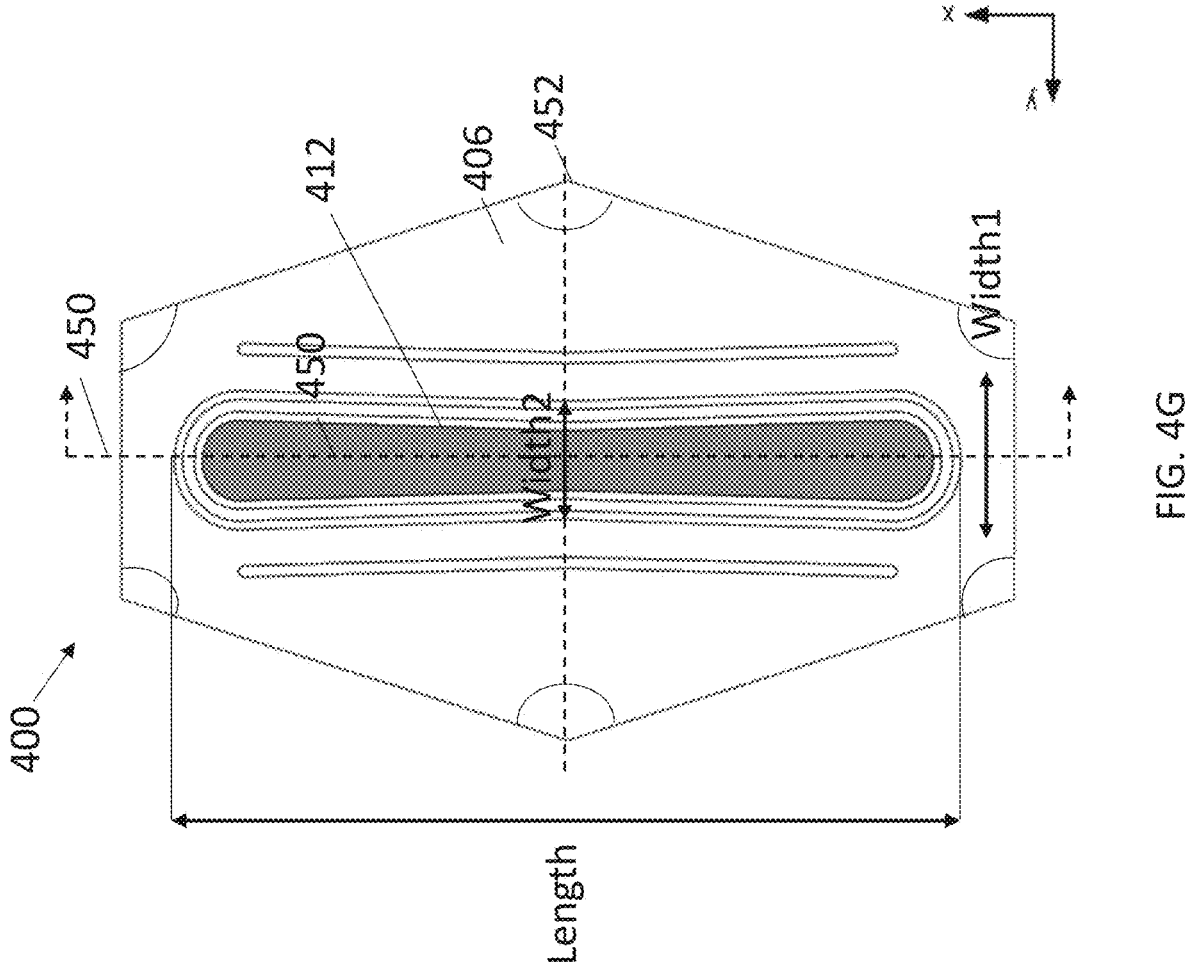
FIG. 4G illustrates a top view of a MUT with multiple piezoelectric layers.

FIG. 4G illustrates a top view of a MUT with multiple piezoelectric layers. The top view shows the electrode which is the furthest (e.g., the largest vertical or z-distance) from the substrate of the MUT device. When viewed from the top (e.g., above the MUT, wherein the MUT is in a negative z-direction from the viewer), the top MUT electrode has a concave shape. In this embodiment, all of the electrodes may have the same shape, as layers of electrodes underneath the top electrode are hidden from view. In this embodiment, at least the top electrode is symmetric with respect to the x- and y-axes. In other embodiments, electrodes disposed beneath the top electrode may have different sizes. In other embodiments, electrodes disposed beneath the top electrode may have different shapes.

In assessing whether an electrode design may yield improved performance at high frequencies, this disclosure defines an electrode aspect ratio. The aspect ratio parameter is related to the ratio R/L and is defined as the ratio of the length of the electrode (the length from the tip of the top head to the base of the bottom head) to twice the characteristic half-width (or two times L). With respect to the embodiments disclosed herein, the concave embodiment of FIG. 4G has aspect ratio 7, the convex embodiment of FIG. 4D has aspect ratio 3, and the concave embodiment of FIG. 4B has aspect ratio 5. Generally, a larger aspect ratio may correlate with increased performance at high frequencies.

When an electrode has a characteristic half-width L that is equal to its radius, it may be stadium-shaped rather than convex or concave. An electrode of given length would have a higher aspect ratio as a concave electrode, a medium aspect ratio as a stadium-shaped electrode, and a lower aspect ratio as a convex electrode. The use of the aspect ratio suggests that a longer convex electrode, or set of electrodes, may be able to achieve similar performance to a shorter concave electrode. Conversely, a smaller concave electrode may be able to be used in place of a larger convex electrode.

Figure 4H:
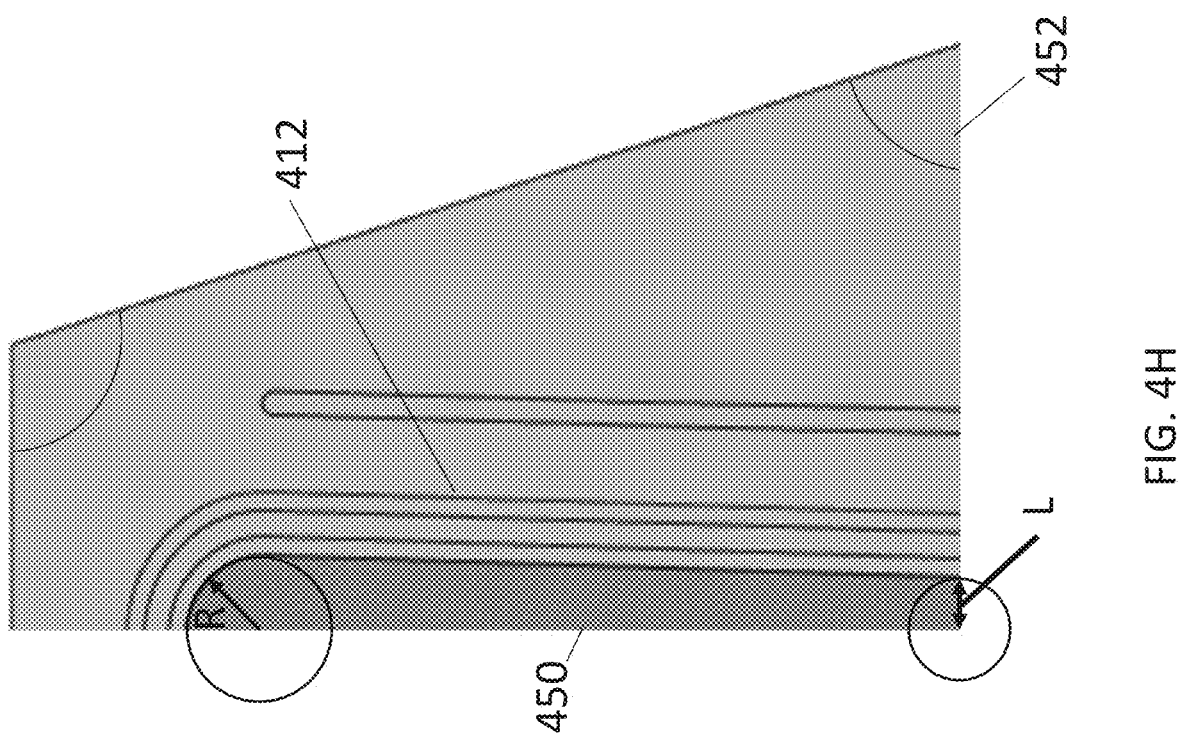
FIG. 4H illustrates a sub-section of the top view of FIG. 4G displayed so that the radius R and characteristic half-width are visible.

FIG. 4H illustrates a sub-section of the top view of FIG. 4G displayed so that the radius R and characteristic half-width are visible. As in FIG. 4C, the value of R is larger than that of L.

Figure 5A:
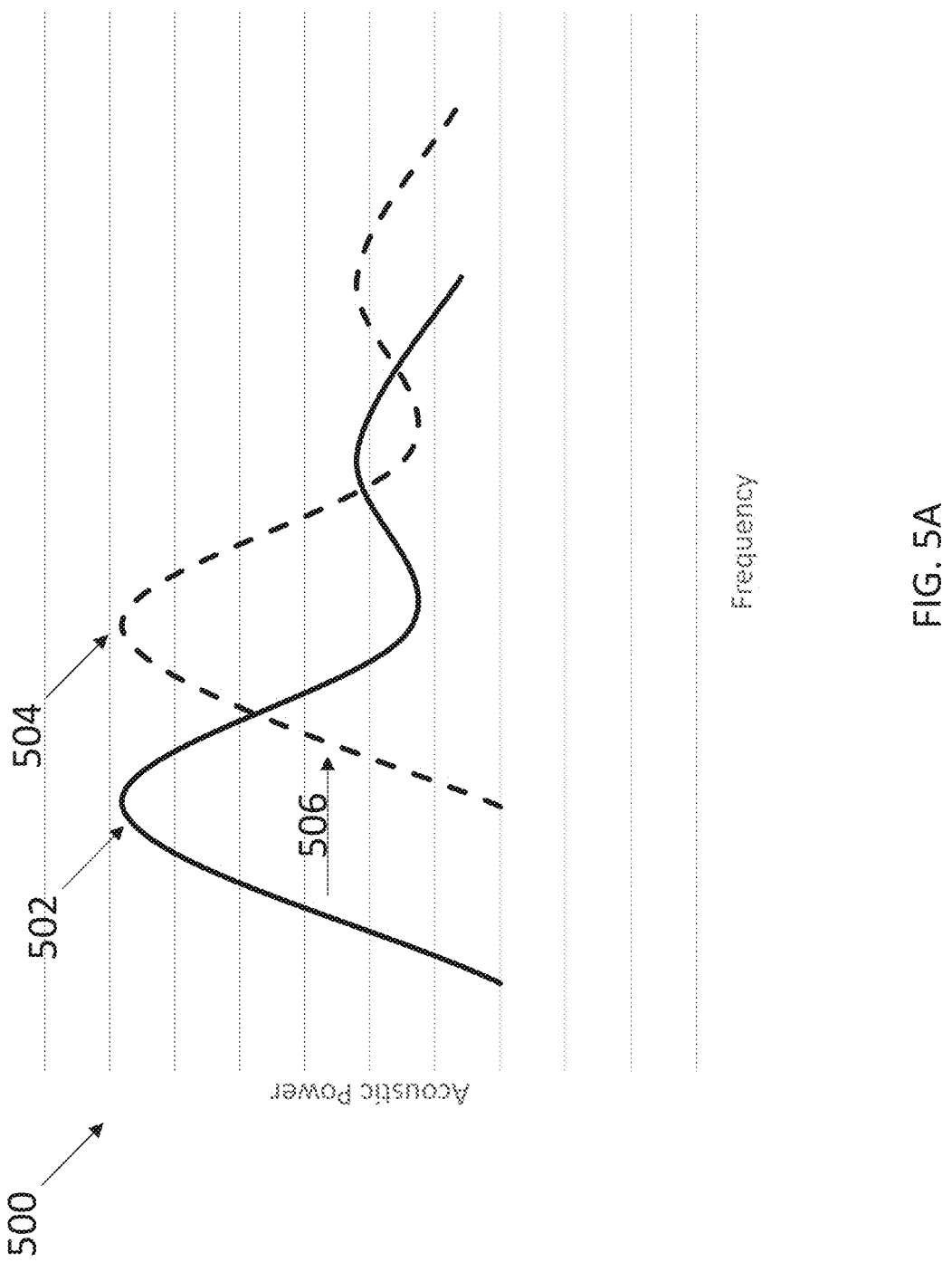
FIG. 5A shows a plot of acoustic responses of a MUT having a concave configuration according to embodiments of the present disclosure.
Figure 5B:
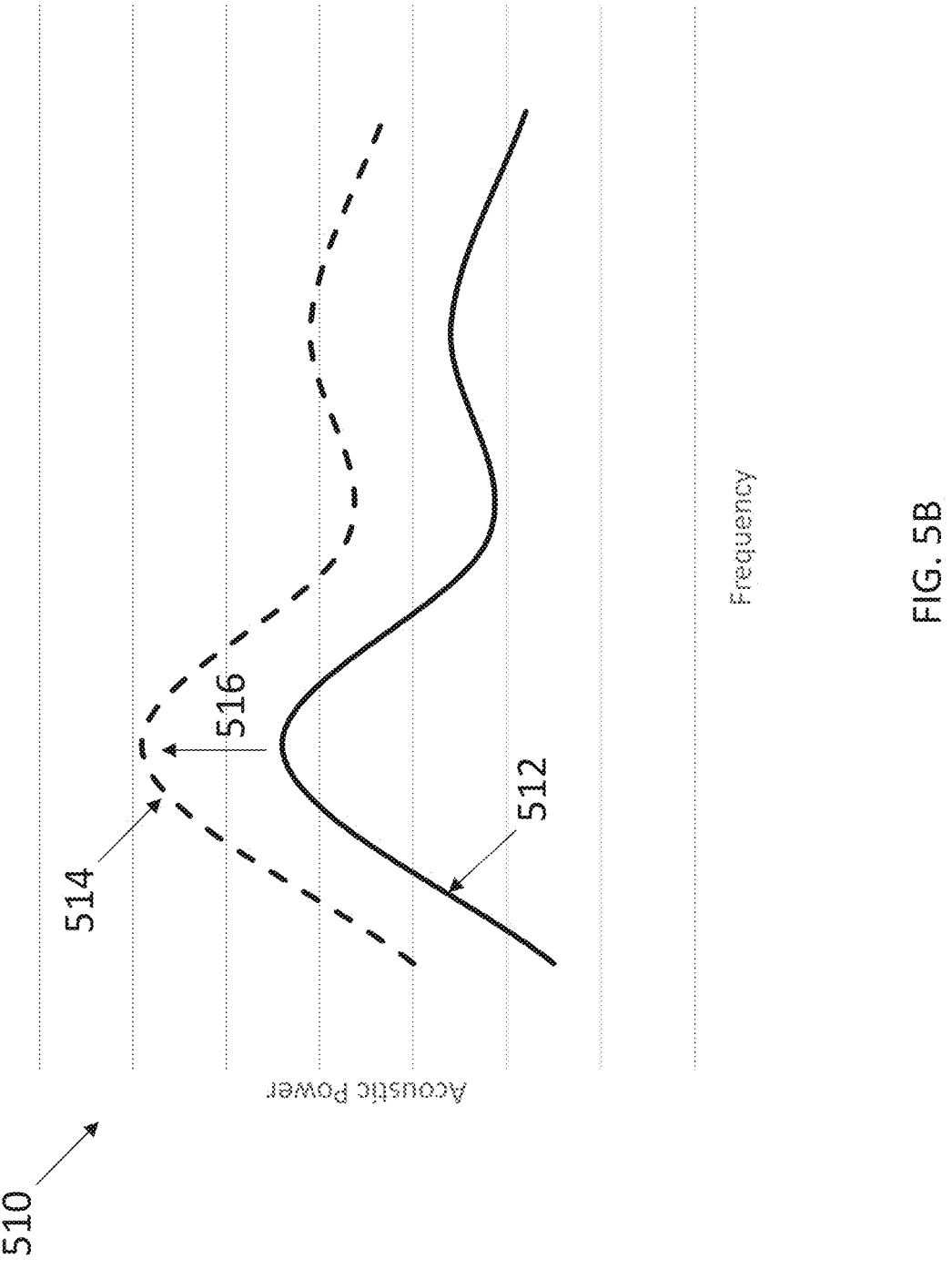
FIG. 5B shows a plot of acoustic responses of a MUT having a convex configuration according to embodiments of the present disclosure.

FIGS. 5A-5B show exemplary idealized plots 500 and 510 of acoustic responses of a MUT having a concave configuration and a MUT having a convex configuration, according to embodiments of the present disclosure. FIG. 5A shows an idealized plot 500 of how acoustic power changes with frequency for a concave MUT 504 (e.g., R/L>1) compared to a MUT 502 with R/L=1. FIG. 5B shows an idealized plot 510 of how acoustic power changes with frequency for a convex MUT 514 (e.g., R/L<1) compared to a MUT 512 with R/L=1. For concave MUT 504, as indicated by arrow 506, as R/L increases, the power-frequency curve shifts to the right compared to MUT 502. For convex MUT 514, as indicated by arrow 516, as R/L decreases, the power-frequency curve shifts to the upwards compared to MUT 512.

Further modifications to the concave or convex MUT geometry, including varying the thickness of the membrane (e.g., a silicon membrane), or adding single or double notches at the periphery of the membrane (such that the membrane behaves more like a pinned beam or spring, rather than a cantilevered beam) may provide further enhanced performance characteristics. Examples of such modifications can be found in U.S. patent application Ser. Nos. 17/018,304 and 15/820,319, which are incorporated herein by reference.

Figure 6A:
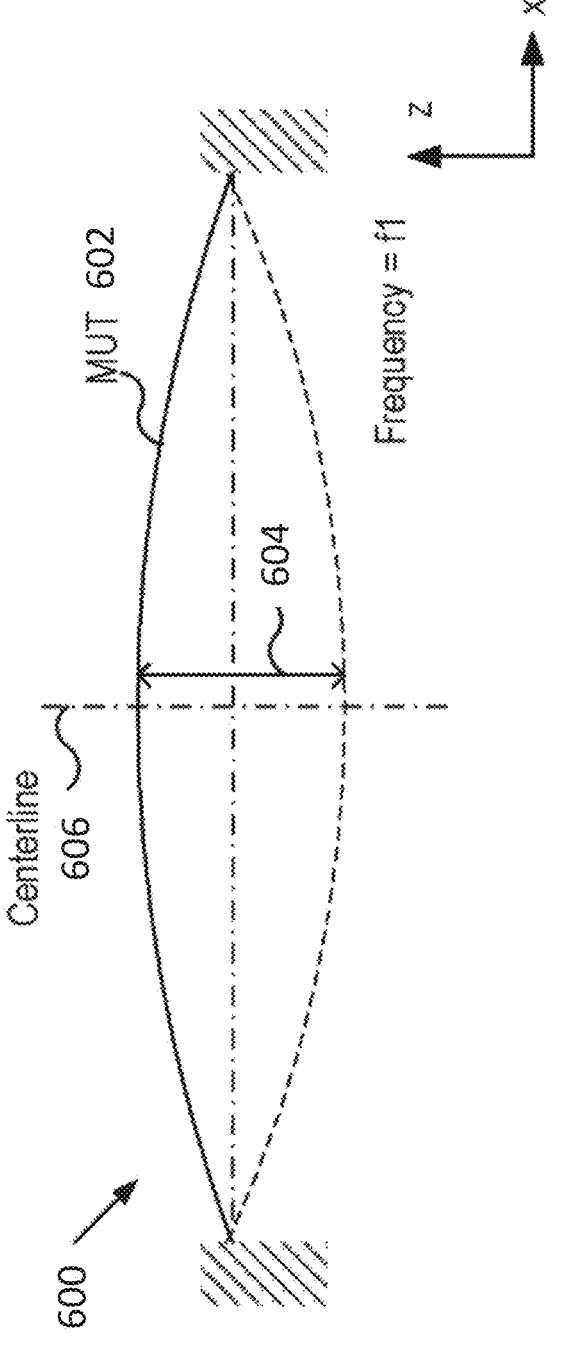
FIGS. 6A-6C show vibrational mode shapes of concave and convex MUTs according to embodiments of the present disclosure.
Figure 6B:
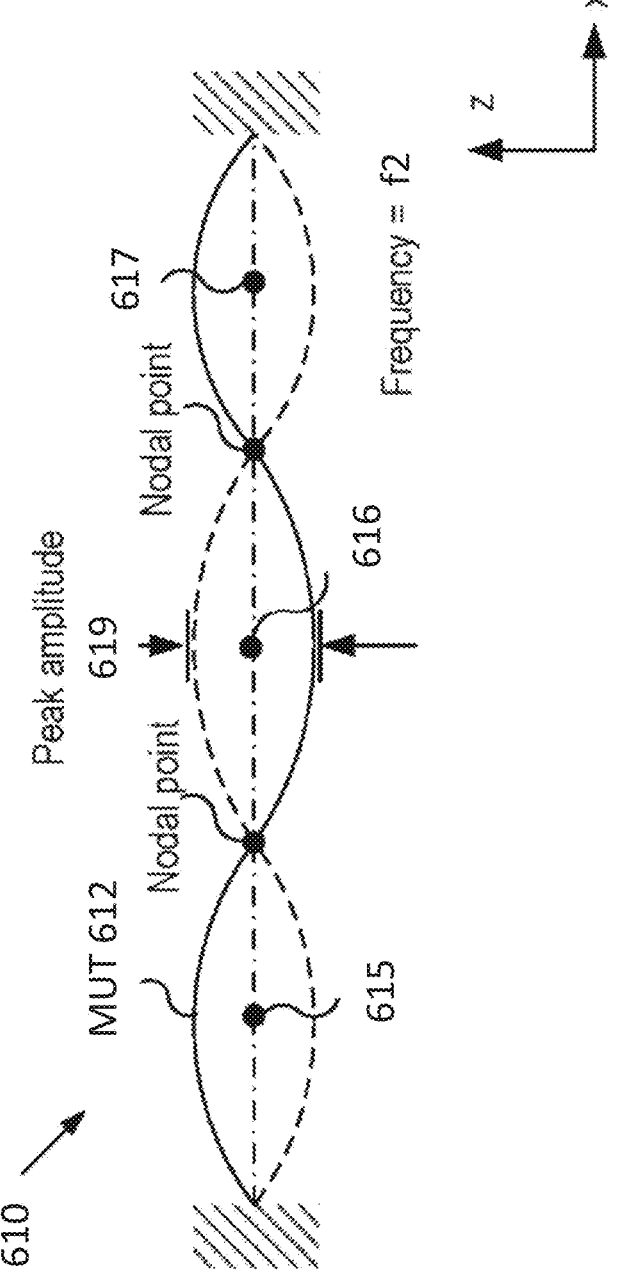
Figure 6C:
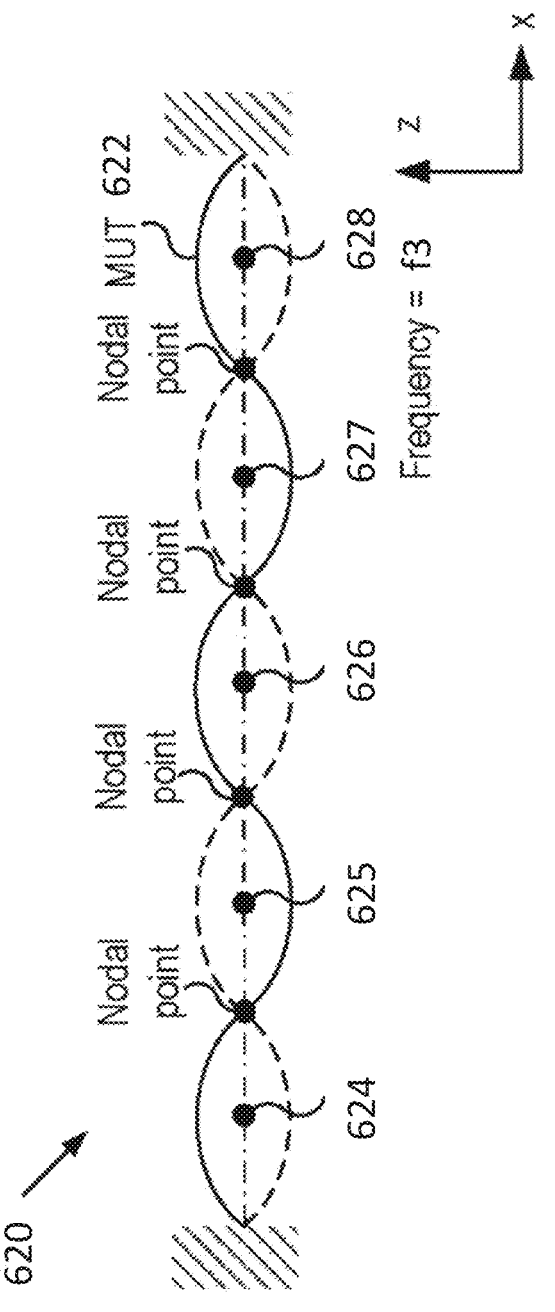

FIGS. 6A-6C show three vibrational modes 600, 610, 620, according to embodiments of the present disclosure. In FIGS. 6A-6C, each of the MUTs 602, 612, and 622, whether concave or convex, is represented by a single line for the purpose of illustration, where each single line shows the curvature of the stack of layers in a MUT. During operation, the stack of layers having the membrane 406, bottom electrode 408, piezoelectric layer 410, and top electrode 412 may move as a single body in the vertical direction, and may be deformed to have the curvature of the single line on the x-z plane. Also, the lines 602, 612, and 622, that correspond to different vibrational modes show the curvatures of the stack at different vibrational modes. In general, the resonance characteristics of a concave MUT and a convex MUT are similar to one another, though local gain may change depending on whether the MUT is concave or convex. In some instances, selection of a convex geometry or a concave geometry may be driven the gain improvements achieved at certain frequencies of interest.

In embodiments, the three vibrational modes 600, 610, and 620 may be associated with three vibrational resonance frequencies, f1, f2, and f3, respectively. In FIGS. 6A-6C, only three vibrational modes are shown. However, it should be apparent to those of ordinary skill in the art that a concave or convex MUT may operate in more than three vibrational resonance modes (or shortly vibrational modes).

In FIG. 6A, the concave or convex MUT 602 may operate in the first vibrational mode 600, where the arrow 604 indicates that the MUT 602 (more specifically, the stack of layers) moves in the vertical direction in the first mode 600. In embodiments, the first vibrational mode 600 may be symmetric, i.e., the mode shape is symmetric with respect to the centerline 606 of the MUT. In embodiments, the shape of the top electrode of the MUT 602 may be symmetric and either be concave or convex, as shown in FIGS. 4B-4E.

In FIG. 6B, the MUT 612 may operate in the second vibrational mode 610. In embodiments, the second vibrational mode 610 may be symmetric, i.e., the mode shape is symmetric with respect to the centerline 606. Hereinafter, the term symmetric vibrational mode refers to a vibrational mode where the locations of the anti-nodal points, such as 615, 616, and 617, (i.e., the peak amplitudes) are arranged symmetrically with respect to a centerline 606, and the centerline 606 represents a line that is parallel to the z-axis and passes through the midpoint of the MUT on the x-axis.

In the second vibrational mode 610, the MUT 612 may have two nodal points and three anti-nodal points (or equivalently, three peak amplitude points) 615, 616, and 617. In embodiments, the shape of the top electrode of the MUT 612 may be symmetric and either be concave or convex, as shown in FIGS. 4B-4E.

In FIG. 6C, the MUT 622 may operate in the third vibrational mode 620. In embodiments, the third vibrational mode 620 may be symmetric, i.e., the mode shape is symmetric with respect to the centerline 606. In the third vibrational mode, the MUT 622 may have four nodal points and five anti-nodal points (i.e. five peak amplitude points) 624, 625, 626, 627, and 628. In embodiments, the shape of the top electrode of the MUT 622 may be symmetric and either be concave or convex, as shown in FIGS. 4B-4E.

In general, the acoustic pressure performance, which refers to the energy of an acoustic pressure wave generated by each MUT at a frequency, may increase as the peak amplitude of the MUT increases at the frequency. However, relative to a convex MUT of same or similar total area, the concave MUT has greater local area distributions at the distal ends compared to the middle (i.e., R>L). As a consequence, relative to a convex MUT of same or similar area, the concave MUT is able to output higher acoustic pressure amplitude, particularly at harmonic frequencies.

It is noted that each of the MUTs 302 in FIG. 3 may be a piezoelectric micromachined ultrasound transducer (pMUT). However, it should be apparent to those of ordinary skill in the art that the transceiver tile 210 may include an array of capacitive micromachined ultrasound transducers (cMUTs), i.e., the piezoelectric elements 302 may be replaced by cMUTs. In such a case, the top electrode of a CMUT may have a shape that is similar to one of shapes of the top electrodes 412, so that the acoustic response of the cMUT is controlled at various vibrational resonance frequencies, based on the principles described in conjunction with FIGS. 4B-6C.

Figure 7A:
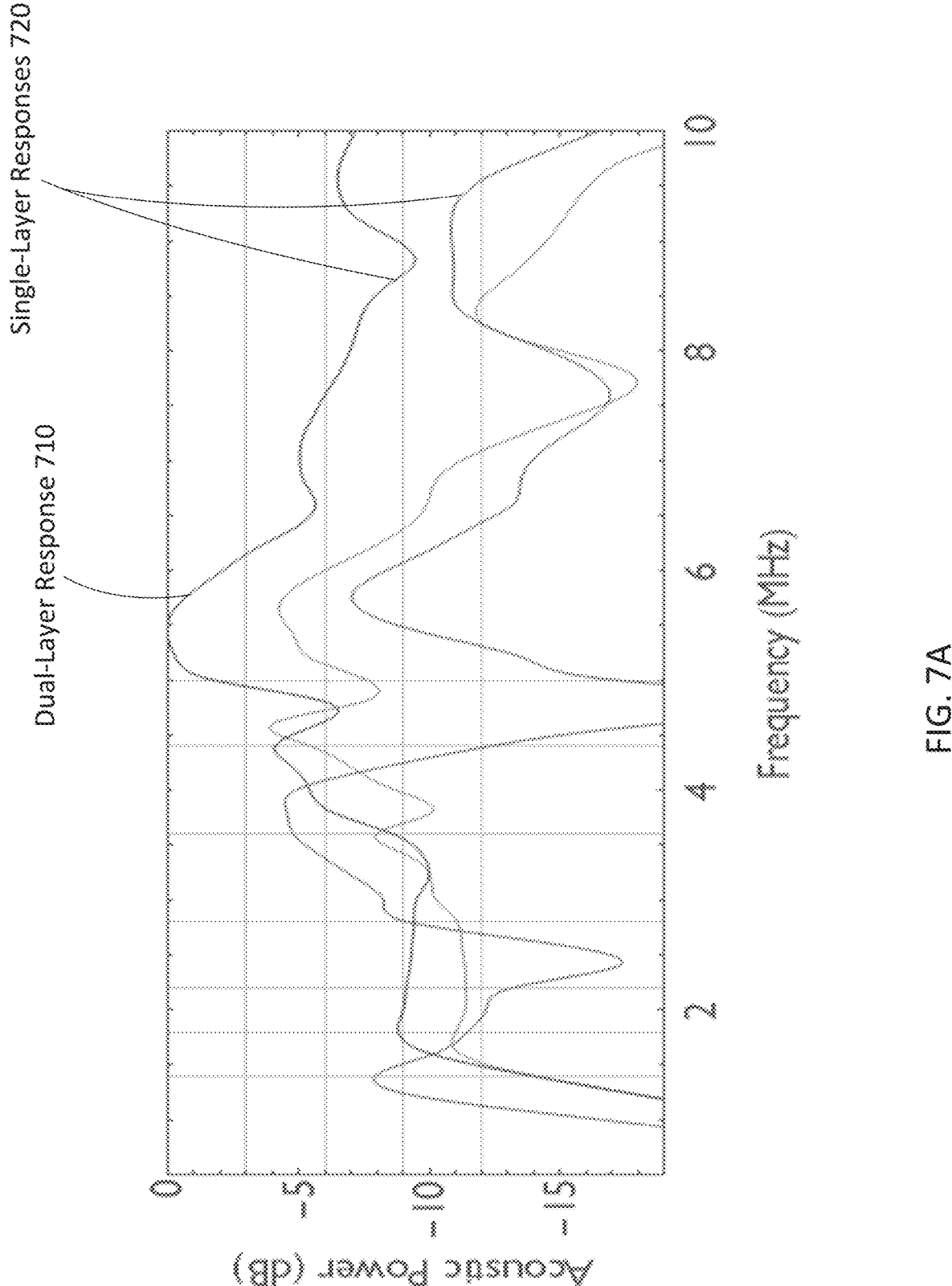
FIG. 7A illustrates a plot of the frequency response of a dual-layer pMUT, compared to frequency responses of single-layer pMUT devices.

FIG. 7A illustrates a plot of the frequency response 710 of a dual-layer pMUT, compared to frequency responses 720 of single-layer pMUT devices. At high frequencies (between about 5 and 10 megahertz (MHz)), the dual-layer pMUT produces acoustic waves with greater acoustic power (in dB) than do the single piezoelectric layer pMUTs.

Figure 7B:
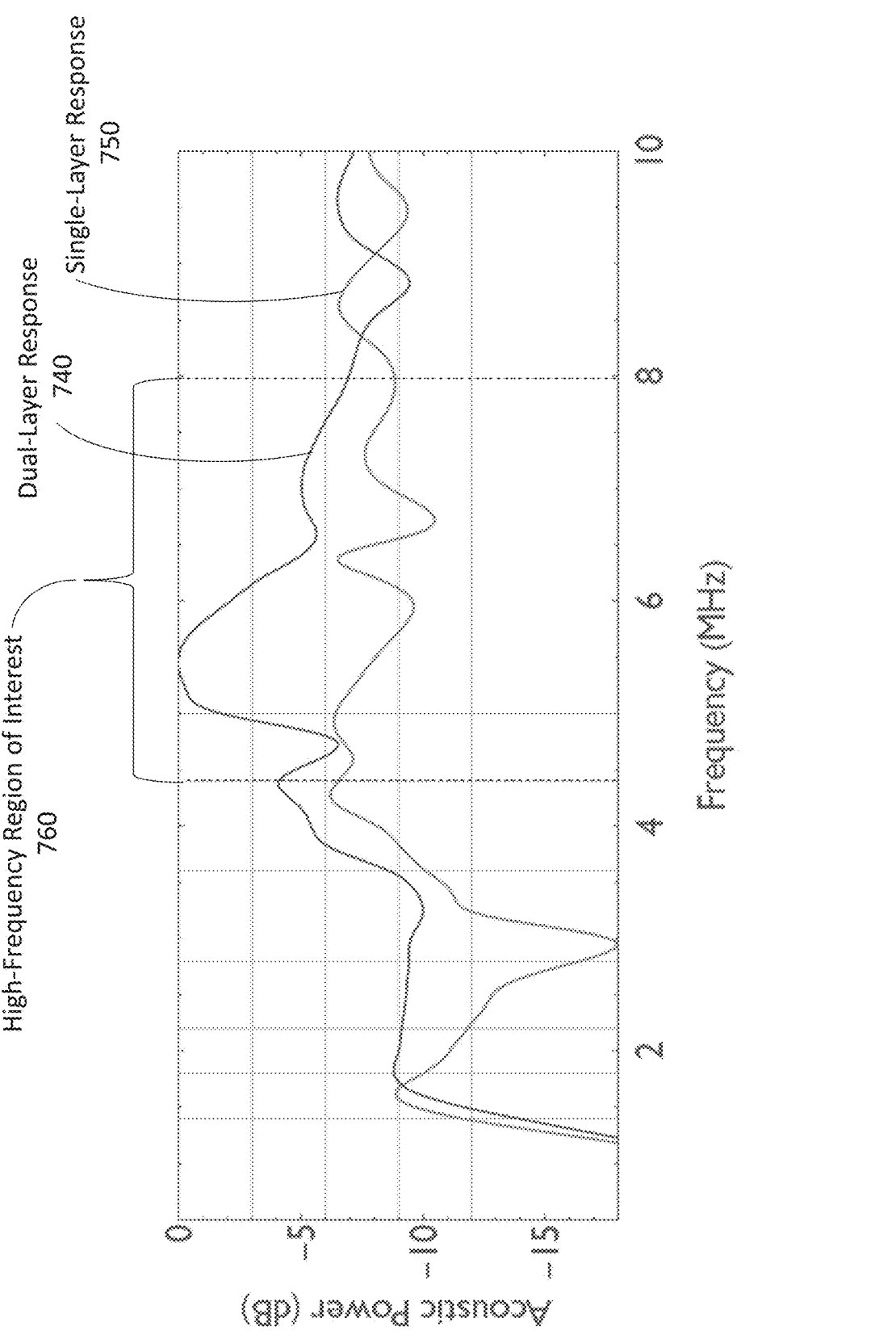
FIG. 7B illustrates a plot of the frequency response of a dual-layer pMUT that has electrodes that are concave in shape, compared to the frequency response of a dual-layer pMUT that has electrodes that are convex in shape.

FIG. 7B illustrates a plot of the frequency response 740 of a dual-layer pMUT that has electrodes that are concave in shape, compared to the frequency response 750 of a dual-layer pMUT that has electrodes that are convex in shape. As can be seen from the plot, the pMUT with concave electrodes outperforms the pMUT with convex electrodes, generating acoustic waves with more power in a high-frequency region of interest 760 between about 4.5 MHz and 8 MHz.

Figure 7C:
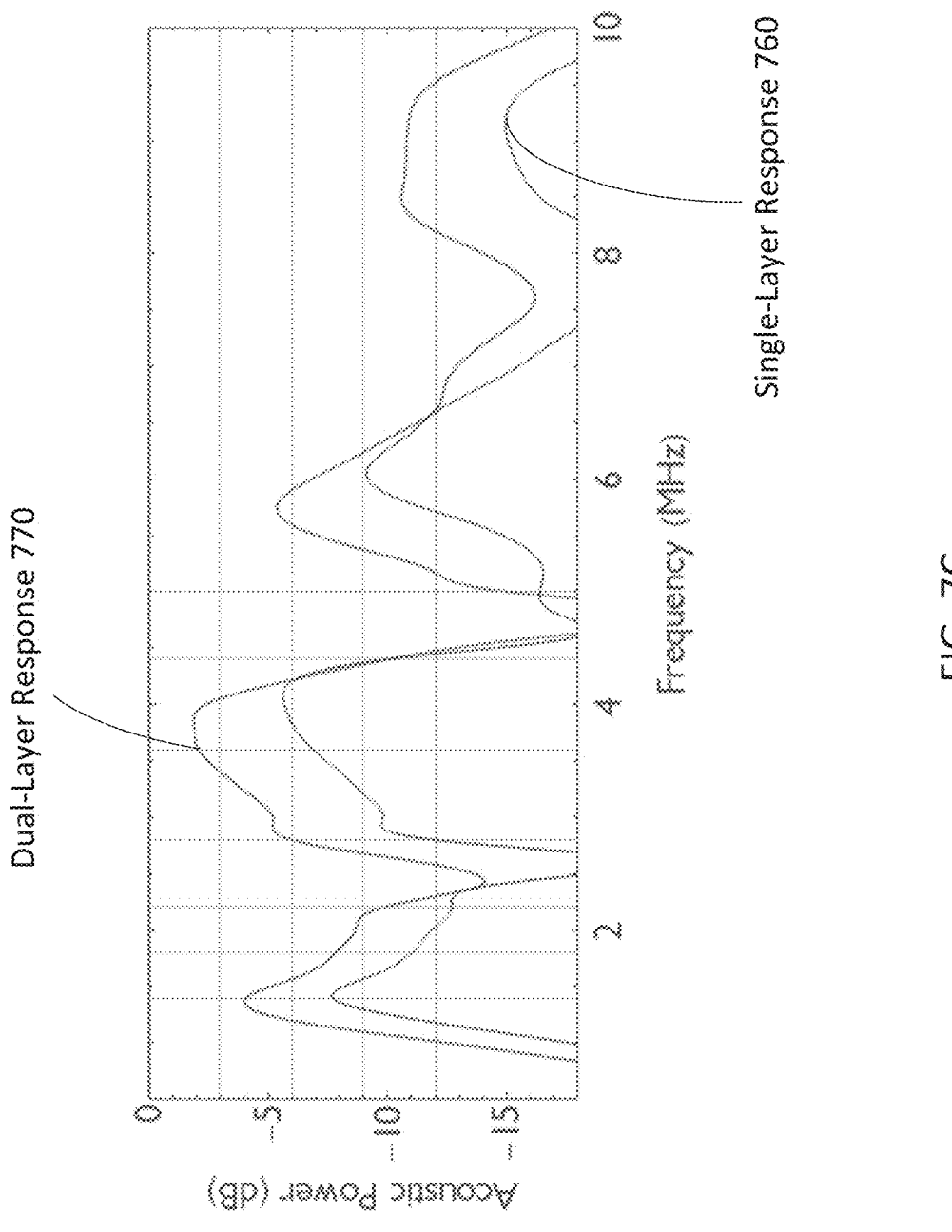
FIG. 7C illustrates a plot of the frequency response of a dual-layer pMUT that has electrodes that are convex in shape, compared to the frequency response of a dual-layer pMUT that has electrodes that are convex in shape.

FIG. 7C illustrates a plot of the frequency response 770 of a dual-layer pMUT that has electrodes that are convex in shape, compared to the frequency response 760 of a single-layer pMUT that has electrodes that are convex in shape. As can be seen from the plot, the dual-layer pMUT outperforms the single-layer pMUT at most frequencies of operation. While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A micromachined ultrasonic transducer (MUT), comprising:
   at least a first piezoelectric layer and a second piezoelectric layer, wherein the first piezoelectric layer is disposed between a first electrode and a second electrode, wherein the second piezoelectric layer is disposed between the second electrode and a third electrode,
   when seen in a top view, at least the first electrode having first and second ends along a first axis, i. wherein one or more of the first end or second end is defined by a radius of curvature R,
   ii. wherein a second axis passes through a midpoint of the first axis, wherein the second axis is normal to the first axis,
   iii. wherein a half-width of the first electrode is defined by a length L measured from the midpoint, in the direction of the second axis, to an outer perimeter of the first electrode,
   iv. wherein a total width of the first electrode at its widest point along the first axis is at least two times L such that the first electrode has a convex shape, and
   v. wherein R/L is less than 1.

2. The MUT of claim 1, wherein the first axis extends along a direction where the first electrode has a longest dimension.

3. The MUT of claim 1, wherein the second axis extends along a direction where the first electrode has a shortest dimension.

4. The MUT of claim 1, further comprising:
   a substrate; and
   a membrane suspending from the substrate.

5. The MUT of claim 4, wherein the piezoelectric layer is formed of at least one of PZT, KNN, PZT-N, PMN-Pt, AlN, Sc-AlN, ZnO, PVDF, and LiNiO₃.

6. A micromachined ultrasonic transducer (MUT), comprising:
   a plurality of piezoelectric layers comprising M piezoelectric layers;
   a plurality of electrodes comprising N electrodes,
   wherein a piezoelectric layer of the plurality of piezoelectric layers with an index m is disposed between a first electrode with an index m and a second electrode with an index m+1, wherein the index m is associated with a vertical distance of the piezoelectric layer;
   when seen in a top view, at least the first electrode having first and second ends along a first axis, i. wherein one or more of the first end or second end is defined by a radius of curvature R,
   ii. wherein a second axis passes through a midpoint of the first axis, wherein the second axis is normal to the first axis,
   iii. wherein a half-width of the first electrode is defined by a length L measured from the midpoint, in the direction of the second axis, to an outer perimeter of the first electrode,
   iv. wherein a total width of the first electrode at its widest point along the first axis is at least two times L such that the first electrode has a convex shape, and
   v. wherein R/L is less than 1.

7. The MUT of claim 6, wherein the first axis extends along a direction where the first electrode has a longest dimension.

8. The MUT of claim 6, wherein the second axis extends along a direction where the first electrode has a shortest dimension.

9. The MUT of claim 6, further comprising:
   a substrate; and
   a membrane suspending from the substrate.

10. The MUT of claim 9, wherein the piezoelectric layer is formed of at least one of PZT, KNN, PZT-N, PMN-Pt, AlN, Sc-AlN, ZnO, PVDF, and LiNiO₃.

11. The MUT of claim 6, wherein N=M+1.

12. The MUT of claim 1, wherein the first end or second end of the first electrode comprises a non-circular curved geometry.

13. The MUT of claim 1, wherein the first, second, and third electrodes have the same shape.

14. The MUT of claim 1, wherein the first, second, and third electrodes have different shapes.

15. The MUT of claim 1, wherein the first, second, and third electrodes are symmetrical with respect to at least one of the first and second axes.

16. The MUT of claim 1, wherein at least one of the first, second, and third electrodes are asymmetrical with respect to at least one of the first and second axes.

17. The MUT of claim 6, wherein the first end or second end of the first electrode comprises a non-circular curved geometry.

18. The MUT of claim 6, wherein the first, second, and third electrodes have the same shape.

19. The MUT of claim 6, wherein the first, second, and third electrodes have different shapes.

20. The MUT of claim 6, wherein the first, second, and third electrodes are symmetric with respect to at least one of the first and second axes.

21. The MUT of claim 6, wherein at least one of the first, second, and third electrodes are asymmetrical with respect to at least one of the first and second axes.

* * * * *